US012577610B2

(12) United States Patent
Mata et al.

(10) Patent No.: US 12,577,610 B2
(45) Date of Patent: Mar. 17, 2026

(54) METHODS FOR DETECTING TARGET NUCLEIC ACIDS BY IN SITU HYBRIDIZATION AND A KIT THEREOF

(71) Applicant: ADVANCED CELL DIAGNOSTICS, INC., Newark, CA (US)

(72) Inventors: Miguel Angel Mata, Newark, CA (US); Aparna Sahajan, Newark, CA (US); Xiao-Jun Ma, Newark, CA (US); Bingqing Zhang, Newark, CA (US); Li Wang, Newark, CA (US); Li-Chong Wang, Newark, CA (US)

(73) Assignee: ADVANCED CELL DIAGNOSTICS, INC., Newark, CA (US)

( * ) Notice: Subject to any disclaimer, the term of this patent is extended or adjusted under 35 U.S.C. 154(b) by 637 days.

(21) Appl. No.: 17/995,561

(22) PCT Filed: Apr. 5, 2021

(86) PCT No.: PCT/US2021/025749
§ 371 (c)(1),
(2) Date: Oct. 5, 2022

(87) PCT Pub. No.: WO2021/207062
PCT Pub. Date: Oct. 14, 2021

(65) Prior Publication Data
US 2023/0151415 A1 May 18, 2023

Related U.S. Application Data

(60) Provisional application No. 63/006,600, filed on Apr. 7, 2020.

(51) Int. Cl.
*C12Q 1/68* (2018.01)
*C12Q 1/6806* (2018.01)
*C12Q 1/6841* (2018.01)

(52) U.S. Cl.
CPC ......... *C12Q 1/6841* (2013.01); *C12Q 1/6806* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Wilhelmus et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,124,246 | A | 6/1992 | Urdea et al. |
| 5,635,352 | A | 6/1997 | Urdea et al. |
| 5,681,697 | A | 10/1997 | Urdea et al. |
| 5,710,264 | A | 1/1998 | Urdea et al. |
| 5,849,481 | A | 12/1998 | Urdea et al. |
| 7,709,198 | B2 | 5/2010 | Luo et al. |
| 8,604,182 | B2 | 12/2013 | Luo et al. |
| 8,951,726 | B2 | 2/2015 | Luo et al. |
| 2003/0129626 | A1 | 7/2003 | Nielsen et al. |
| 2008/0038725 | A1 | 2/2008 | Luo et al. |
| 2009/0081688 | A1 | 3/2009 | Luo et al. |
| 2012/0100540 | A1 | 4/2012 | Wu et al. |
| 2013/0130265 | A1 | 5/2013 | Parikh et al. |
| 2013/0150264 | A1 | 6/2013 | Nielson et al. |
| 2013/0203055 | A1 | 8/2013 | Aurich-Costa |
| 2017/0101672 | A1 | 4/2017 | Luo et al. |
| 2017/0336303 | A1 | 11/2017 | Chafin et al. |

FOREIGN PATENT DOCUMENTS

| | | |
|---|---|---|
| CN | 1450170 A | 10/2003 |
| CN | 107312838 | 11/2017 |
| CN | 109207612 | 1/2019 |
| WO | WO 90/02173 | 3/1990 |
| WO | WO 1999/057309 | 11/1999 |
| WO | WO 2006/102070 | 9/2006 |
| WO | WO-2010097707 A1 | 9/2010 |
| WO | WO 2011/153354 | 12/2011 |
| WO | WO-2012110646 A1 | 8/2012 |
| WO | WO-2012110899 A2 | 8/2012 |
| WO | WO-2013082499 A1 | 6/2013 |
| WO | WO 2016/120195 | 8/2016 |
| WO | WO 2017/066211 | 4/2017 |
| WO | WO 2019/199643 | 10/2019 |

OTHER PUBLICATIONS

International Search Report and Written Opinion for PCT/US2021/025749. Mailed Jul. 20, 2021. 10 pages.
"Cervical Cytology Practice Guidelines" Approved by the American Society of Cytopathology (ASC) Executive Board, Nov. 10, 2000. 26 pages.
"Non-Gynecological Cytology Practice Guideline" American Society of Cytopathology, Adopted by the ASC executive board Mar. 2, 2004. 26 pages.
Anderson et al., Fully Automated RNAscope In Situ Hybridization Assays for Formalin-Fixed Paraffin-Embedded Cells and Tissues. J Cell Biochem. Oct. 2016;117(10):2201-8.
Bartel. Metazoan MicroRNAs. Cell. Mar. 22, 2018;173(1):20-51.
Brown et al., New technologies for cervical cancer screening. Best Pract Res Clin Obstet Gynaecol. Apr. 2012;26(2):233-42.

(Continued)

*Primary Examiner* — Heather Calamita

(74) *Attorney, Agent, or Firm* — Casimir Jones, S.C.; Anne M. Reynolds

(57) ABSTRACT

A method of detecting target nucleic acids, including small non-coding RNAs (sncRNAs), microRNAs (miRNAs), small interfering RNAs (siRNAs), PIWI-interacting RNA (piRNA), or antisense oligonucleotides (ASO) molecules, in a cell, comprising a post-fixation step using an aldehyde-containing fixative after the initial fixation step prior to in situ hybridization.

18 Claims, 10 Drawing Sheets

(56) References Cited

OTHER PUBLICATIONS

Figure 1:
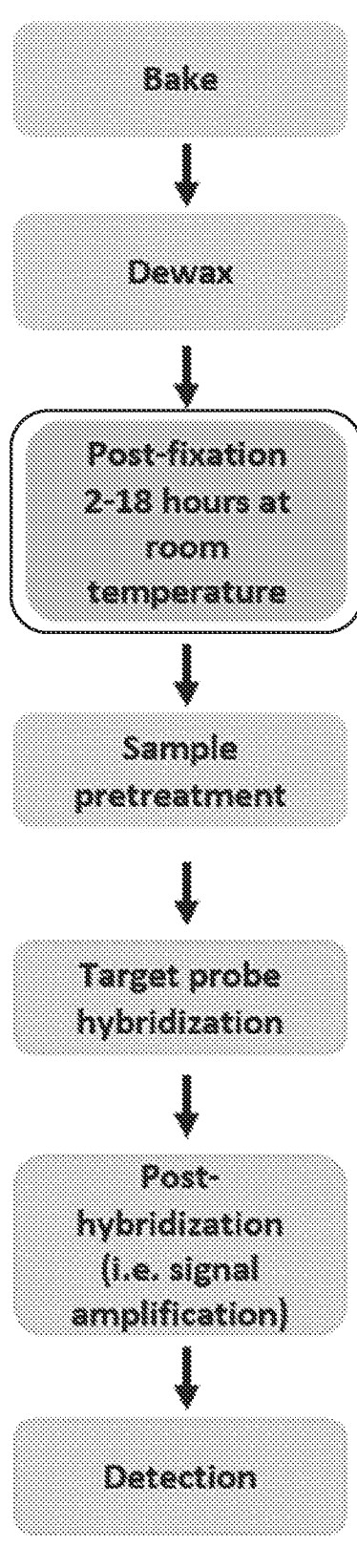

Burns et al., Choice of Fixative is Crucial to Successful Immunohistochemical Detection of Phosphoproteins in Paraffin-embedded Tumor Tissues. J. Histochem. Cytochem. Mar. 2009; 57(3):257-264.

Daniel et al., FastTag Nucleic Acid Labeling System: a versatile method for incorporating haptens, fluorochromes and affinity ligands into DNA, RNA and oligonucleotides. Biotechniques. Mar. 1998;24(3):484-9.

Dey, "Cytology Sample Procurement, Fixation and Processing" in Basic and Advanced Laboratory Techniques in Histopathology and Cytology, Springer, Singapore. 2018. 121-132.

Hanna et al., The Potential for microRNA Therapeutics and Clinical Research. Front Genet. May 16, 2019:10:478. 1-6.

Hicks et al., In situ hybridization in the pathology laboratory: general principles, automation, and emerging research applications for tissue-based studies of gene expression. J Mol Histol. Aug. 2004;35(6):595-601.

Kalof et al., Our approach to squamous intraepithelial lesions of the uterine cervix. J Clin Pathol. May 2007;60(5):449-55.

Kothmaier et al., Comparison of formalin-free tissue fixatives: a proteomic study testing their application for routine pathology and research. Arch Pathol Lab Med. Jun. 2011;135(6):744-52.

Lykidis et al., Novel zinc-based fixative for high quality DNA, RNA and protein analysis. Nucleic Acids Res. 2007;35(12):e85. 1-10.

Manafi et al., Fluorogenic and chromogenic substrates used in bacterial diagnostics. Microbiol Rev. Sep. 1991;55(3):335-48.

Moffitt et al., High-throughput single-cell gene-expression profiling with multiplexed error-robust fluorescence in situ hybridization. Proc Natl Acad Sci U S A. Sep. 27, 2016;113(39):11046-51.

Molnar et al., miRNAs control gene expression in the single-cell alga Chlamydomonas reinhardtii. Nature, 2007, 447(7148), 1126-1130.

Nadji et al., Immunohistochemistry of tissue prepared by a molecular-friendly fixation and processing system. Appl Immunohistochem Mol Morphol. Sep. 2005;13(3):277-82.

Nietner et al., Systematic comparison of tissue fixation with alternative fixatives to conventional tissue fixation with buffered formalin in a xenograft-based model. Int. J. Pathol. 2012; 461:259-269.

Paavilainen et al., The impact of tissue fixatives on morphology and antibody-based protein profiling in tissues and cells. J Histochem Cytochem. Mar. 2010;58(3):237-46.

Pena et al., miRNA in situ hybridization in formaldehyde and EDC-fixed tissues. Nat Methods. Feb. 2009;6(2):139-41.

Renwick et al., Multicolor microRNA FISH effectively differentiates tumor types. J Clin Invest. Jun. 2013;123(6):2694-702.

Schoch et al., Antisense Oligonucleotides: Translation from Mouse Models to Human Neurodegenerative Diseases. Neuron. Jun. 21, 2017;94(6):1056-1070.

Sidorenko et al., Correlated cleavage of single- and double-stranded substrates by uracil-DNA glycosylase. FEBS Lett. Feb. 6, 2008;582(3):410-4.

Van Essen et al., Alcohol based tissue fixation as an alternative for formaldehyde: influence on immunohistochemistry. J Clin Pathol. Dec. 2010;63(12):1090-4.

Vince et al., Quantitative comparison of immunohistochemical staining intensity in tissues fixed in formalin and Histochoice. Anal Cell Pathol. 1997;15(2):119-29.

Wang et al., RNAscope: a novel in situ RNA analysis platform for formalin-fixed, paraffin-embedded tissues. J Mol Diagn. Jan. 2012;14(1):22-9.

Watts et al., Silencing disease genes in the laboratory and the clinic. J Pathol. Jan. 2012;226(2):365-79.

Waxman et al., Revised terminology for cervical histopathology and its implications for management of high-grade squamous intraepithelial lesions of the cervix. Obstet Gynecol. Dec. 2012;120(6):1465-71.

Shichiri, Motoharu et al., Analyses of the chromosome morphological changes during FISH treatment and the preserving effect of the formaldehyde re-fixation, Chromosome science, 2006, vol. 9, No. 4, p. 122, 0-21.

Mmu-miR-1a-3p

Untreated        Formaldehyde post-fixed

12%        24%        37%

Mmu-miR-132-3p

Untreated       NBF post-fixed

Mmu-miR-1a-3p

Untreated         NBF post-fixed

Mmu-miR-132-3p

Untreated          NBF post-fixed

Mmu-miR-122-5p

Untreated          NBF post-fixed

Mmu-let-7

Untreated      NBF post-fixed

Hs-TBP

Untreated | NBF post-fixed

Mm-POLR2A

Untreated                NBF post-fixed

Mm-POLR2A

METHODS FOR DETECTING TARGET NUCLEIC ACIDS BY IN SITU HYBRIDIZATION AND A KIT THEREOF

CROSS-REFERENCE TO RELATED APPLICATIONS

This application is a U.S. national stage filing under 35 U.S.C. § 371 of International Patent Application No. PCT/US2021/025749, filed on Apr. 5, 2021, which claims priority to and the benefit of U.S. Provisional Patent Application No. 63/006,600, filed on Apr. 7, 2020.

1. FIELD

Provided herein, in some embodiments, is a method for preparing a biological sample for in situ hybridization, including but not limited to detecting small non-coding RNA (sncRNA), microRNA (miRNA), PIWI-interacting RNA (piRNA), small interfering RNA (siRNA), or antisense oligonucleotides (ASO) molecules. Further provided is a method for detecting a target nucleic acid in a cell. Also provided herein, in certain embodiments, is a kit for carrying out the methods and biological samples that are prepared by the methods.

2. BACKGROUND

In situ hybridization (ISH) is a technique that allows for precise detection of a specific segment of a nucleic acid within a histologic section. The underlying basis of ISH is that nucleic acids, if preserved adequately within a histologic specimen, can be detected through the application of a complementary nucleic acid strand to which a reporter molecule is attached. Target nucleic acids can be deoxyribonucleic acid (DNA) or ribonucleic acid (RNA).

Different types of RNA exist in a cell, including (i) messenger RNA (mRNA), which encodes amino acid sequence of a polypeptide; (ii) transfer RNA (tRNA), which brings amino acids to ribosomes during translation; (iii) ribosomal RNA (rRNA), which makes up the ribosomes, the organelles that translate the mRNA; and (iv) sncRNA, which is involved in various RNA processing. Specifically, sncRNA, miRNA, siRNA, piRNA, and ASO, are of significant importance in research, diagnostics, and drug development (see, e.g., Hanna et al., Frontiers in Genetics, 10, 1-6, 2019; Watts et al., Journal of Pathology, 226(2), 365-379, 2012). Methods demonstrating improved detection sensitivity for RNAs, especially small RNAs, within the tissue microenvironment as determined by RNA ISH technology is needed.

Despite the critical roles of small nucleic acids in diverse biological processes, detection of these species has been problematic. Preservation of tissue specimens for histopathology has relied on cross-linking proteins and nucleic acids using chemical fixatives. This fixation strategy is compatible with current RNA ISH technology for the detection of long messenger RNA (mRNA) species. However, this approach inadequately cross-links small nucleic acids leading to release and dispersal of these species from tissues resulting in poor detection by ISH assays. Therefore, a need exists for new compositions and methods for detecting a broader range of nucleic acid molecules by ISH.

3. SUMMARY

In one aspect, provided herein is a method for preparing a biological sample for in situ hybridization comprising: i. a first fixation step comprising fixing the biological sample with an agent; and ii. a post-fixation step after the first fixation step prior to in situ hybridization comprising fixing the biological sample with an aldehyde-containing fixative.

In some embodiments, the method can be used to prepare a biological sample for RNA in situ hybridization. In some embodiments, the method can be used to prepare a biological sample for DNA in situ hybridization.

In some embodiments, the in situ hybridization methods of the present disclosure can be used to detect nucleic acids comprising less than 100 nucleotides. In some embodiments, the RNA in situ hybridization methods can be used to detect RNA comprising less than 50 nucleotides. In some embodiments, the RNA in situ hybridization methods can be used to detect RNA comprising between 15 and 40 nucleotides.

In some embodiments, the RNA in situ hybridization methods of the present disclosure can be used to detect small non-coding RNA (sncRNA). In some embodiments, the RNA in situ hybridization methods can be used to detect microRNA (miRNA), small interfering RNA (siRNA), or PIWI-interacting RNA (piRNA), antisense oligonucleotides (ASO) molecules. In some embodiments, the RNA in situ hybridization methods can be used to detect endogenous RNA. In some embodiments, the RNA in situ hybridization methods can be used to detect exogenous RNA.

In some embodiments, the biological sample is a tissue specimen or is derived from a tissue specimen. In other embodiments, the biological sample is a blood sample or is derived from a blood sample. In other embodiments, the biological sample is a cytological sample or is derived from a cytological sample. In other embodiments, the biological sample is cultured cells. In other embodiments, the biological sample is an exosome.

In some embodiments, the agent in the first fixation step is selected from a group consisting of formaldehyde, glutaraldehyde, alcohol (methanol, ethanol), and acetone.

In other embodiments, the aldehyde-containing fixative in the post-fixation step is selected from a group consisting of formaldehyde or glutaraldehyde.

In some embodiments, the aldehyde-containing fixative comprises about 5% to about 50% formaldehyde. In certain embodiments, the aldehyde-containing fixative comprises less than about 12% formaldehyde. In some embodiments, the post-fixation step comprises fixing the biological sample with the aldehyde-containing fixative for more than about 2, 3, 4, 5, 6, 7, 8, 9, 10, 11, 12, 13, 14, 15, 16, 17, or 18 hours.

In certain embodiments, the aldehyde-containing fixative comprises at least about 12% formaldehyde, and the post-fixation step comprises fixing the biological sample with the aldehyde-containing fixative for about 2 hours. In certain embodiments, the aldehyde-containing fixative comprises about 12% to about 37% formaldehyde, and the post-fixation step comprises fixing the biological sample with the aldehyde-containing fixative for about 2 hours.

In some embodiments, a biological sample is prepared according to the above methods.

In another aspect, embodiments of the present disclosure include methods for detecting a target nucleic acid in a cell, comprising: (i) preparing a biological sample; (ii) providing at least one set of one or more target probe(s) capable of hybridizing to said target nucleic acid; (iii) providing a signal-generating complex capable of hybridizing to said set of one or more target probe(s), said signal-generating complex comprises a nucleic acid component capable of hybridizing to said set of one or more target probe(s) and a label probe; (iv) hybridizing said target nucleic acid to said set of one or more target probe(s); and (v) capturing the signal-generating complex to said set of one or more target probe(s) and thereby capturing the signal-generating complex to said target nucleic acid.

In certain embodiments, each of the target probe(s) comprises a target (T) section and a label (L) section. In some embodiments, the T section is a nucleic acid sequence complementary to a section on the target nucleic acid and the L section is a nucleic acid sequence complementary to a section on the nucleic acid component of the signal generating complex. In another specific embodiments, the T sections of the one or more target probe(s) are complementary to non-overlapping regions of the target nucleic acid, and the L sections of the one or more target probe(s) are complementary to non-overlapping regions of the nucleic acid component of the generating complex.

In some embodiments, the target nucleic acid comprises less than about 100 nucleotides. In other embodiments, the target nucleic acid is RNA comprising less than about 50 nucleotides. In other embodiments, the target nucleic acid is RNA comprising from about 15 to about 40 nucleotides.

In some embodiments, the target nucleic acid is sncRNA. In some embodiments, the target nucleic acid is miRNA, siRNA, piRNA, or ASO. In some embodiments, the target nucleic acid is an endogenous nucleic acid. In other embodiments, the target nucleic acid is an exogenous nucleic acid.

In some embodiments, the method is used for identifying tissue or cell type. In other embodiments, the method is used for determining developmental stages. In other embodiments, the method is used for characterizing adult tissue. In other embodiments, the method is used for diagnosing a disease or disorder based on the expression of one or more altered small RNA or the presence of pathogen-derived small RNA. In other embodiments, the method is used for monitoring or determining the effectiveness of a small RNA or oligonucleotide-based therapy.

In another aspect, embodiments of the present disclosure include methods of preserving a target nucleic acid in a previously fixed sample for in situ detection of a target nucleic acid, comprising applying an aldehyde-containing fixative to said sample before conducting an in situ hybridization detection assay with a set of one or more probes hybridizing to said target nucleic acid.

In another aspect, provided herein is a method of in situ detection of a target nucleic acid in a previously fixed sample, comprising (i) applying an aldehyde-containing fixative to the sample, and (ii) conducting in situ hybridization detection assay with a set of one or more probes hybridizing to said target nucleic acid.

In some embodiments, the target nucleic acid comprises less than about 100 nucleotides. In other embodiments, the target nucleic acid is RNA comprising less than about 50 nucleotides. In other embodiments, the target nucleic acid is RNA comprising from about 15 to about 40 nucleotides.

In some embodiments, the biological sample is a tissue specimen or is derived from a tissue specimen. In other embodiments, the biological sample is a blood sample or is derived from a blood sample. In other embodiments, the biological sample is a cytological sample or is derived from a cytological sample. In other embodiments, the biological sample is cultured cells. In other embodiments, the biological sample is an exosome.

In some embodiments, the aldehyde-containing fixative in the post-fixation step comprises formaldehyde or glutaraldehyde.

In some embodiments, the aldehyde-containing fixative comprises about 5% to about 50% formaldehyde. In certain embodiments, the aldehyde-containing fixative comprises less than about 12% formaldehyde, and the post-fixation step comprises fixing the biological sample with the aldehyde-containing fixative for more than about 2, 3, 4, 5, 6, 7, 8, 9, 10, 11, 12, 13, 14, 15, 16, 17, or 18 hours. In certain embodiments, the aldehyde-containing fixative comprises at least about 12% formaldehyde, and the post-fixation step comprises fixing the biological sample with the aldehyde-containing fixative for about 2 hours. In specific embodiments, the aldehyde-containing fixative comprises about 12% to about 37% formaldehyde, and the post-fixation step comprises fixing the biological sample with the aldehyde-containing fixative for about 2 hours.

In some embodiments, the set of probes comprises one or more target probe(s) capable of hybridizing to said target nucleic acid, and the method further comprises: (a) providing a signal-generating complex capable of hybridizing to said set of one or more target probe(s), said signal-generating complex comprises a nucleic acid component capable of hybridizing to said set of one or more target probe(s) and a label probe; (b) hybridizing said target nucleic acid to said set of one or more target probe(s); and (c) capturing the signal-generating complex to said set of one or more target probe(s) and thereby capturing the signal-generating complex to said target nucleic acid.

In some embodiments, each of the target probe(s) comprises a target (T) section and a label (L) section. In certain embodiments, T section is a nucleic acid sequence complementary to a section on the target nucleic acid and the L section is a nucleic acid sequence complementary to a section on the nucleic acid component of the signal generating complex. In certain embodiments, the T sections of the one or more target probe(s) are complementary to non-overlapping regions of the target nucleic acid, and the L sections of the one or more target probe(s) are complementary to non-overlapping regions of the nucleic acid component of the generating complex.

In another aspect, a kit for in situ detection of a target nucleic acid in a cell comprises (i) an agent for fixing a biological sample comprising the cell; (ii) an aldehyde-containing fixative for fixing the biological sample; (iii) an agent for performing in situ hybridization; and (iv) an instruction indicating that the aldehyde-containing fixative is used after the agent in component (i). In some embodiments, the kit for in situ detecting a target nucleic acid in a cell comprises an aldehyde-containing fixative for fixing the biological sample, and an agent for performing in situ hybridization.

In some embodiments, the agent in component (i) is selected from a group consisting of formaldehyde, glutaraldehyde, alcohol (methanol, ethanol), and acetone. In other embodiments, the aldehyde-containing fixative comprises formaldehyde or glutaraldehyde.

In some embodiments, the aldehyde-containing fixative comprises about 5% to about 50% formaldehyde. In certain embodiments, the aldehyde-containing fixative comprises at least about 12% formaldehyde. In certain embodiments, the aldehyde-containing fixative comprises about 12% to about 37% formaldehyde.

In some embodiments, the agent for performing in situ hybridization comprises at least one set of one or more target probe(s) capable of hybridizing to said target nucleic acid; and a signal-generating complex capable of hybridizing to said set of one or more target probe(s). In certain embodiments, said signal-generating complex comprises a nucleic acid component capable of hybridizing to said set of one or more target probe(s) and a label probe.

In some embodiments, each of the target probe(s) comprises a target (T) section and a label (L) section. In certain embodiments, the T section is a nucleic acid sequence complementary to a section on the target nucleic acid and the L section is a nucleic acid sequence complementary to a section on the nucleic acid component of the signal generating complex. In certain embodiments, the T sections of the one or more target probe(s) are complementary to non-overlapping regions of the target nucleic acid, and the L sections of the one or more target probe(s) are complementary to non-overlapping regions of the nucleic acid component of the generating complex.

In some embodiments, the kit further comprises a tool for obtaining a biological sample. In certain embodiments, the biological sample is a tissue specimen or is derived from a tissue specimen. In certain embodiments, the biological sample is a blood sample or is derived from a blood sample. In certain embodiments, the biological sample is a cytological sample or is derived from a cytological sample. In certain embodiments, the biological sample is cultured cells. In certain embodiments, the biological sample is an exosome.

In some embodiments, the target nucleic acid comprises less than about 100 nucleotides. In other embodiments, the target nucleic acid is RNA comprising less than 50 nucleotides. In other embodiments, the target nucleic acid is RNA comprising from about 15 to about 40 nucleotides. In some embodiments, the target nucleic acid is sncRNA. In other embodiments, the target nucleic acid is miRNA, siRNA, piRNA, or ASO. In other embodiments, the target nucleic acid is an endogenous or exogenous.

In some embodiments, the kit is used for identifying tissue or cell type. In other embodiments, the kit is used for determining developmental stages. In other embodiments, the kit is used for characterizing adult tissue. In other embodiments, the kit is used for diagnosing a disease or disorder based on the expression of one or more altered small RNA or the presence of pathogen-derived small RNA. In other embodiments, the method is used for monitoring or determining the effectiveness of a small RNA-based therapy.

4. BRIEF DESCRIPTION OF THE FIGURES

FIG. 1 shows the integration of a post-fixation step in a standard RNA ISH workflow. The post-fixation step that is absent from standard RNA ISH workflow is labeled with double boxes.

Figure 2A:
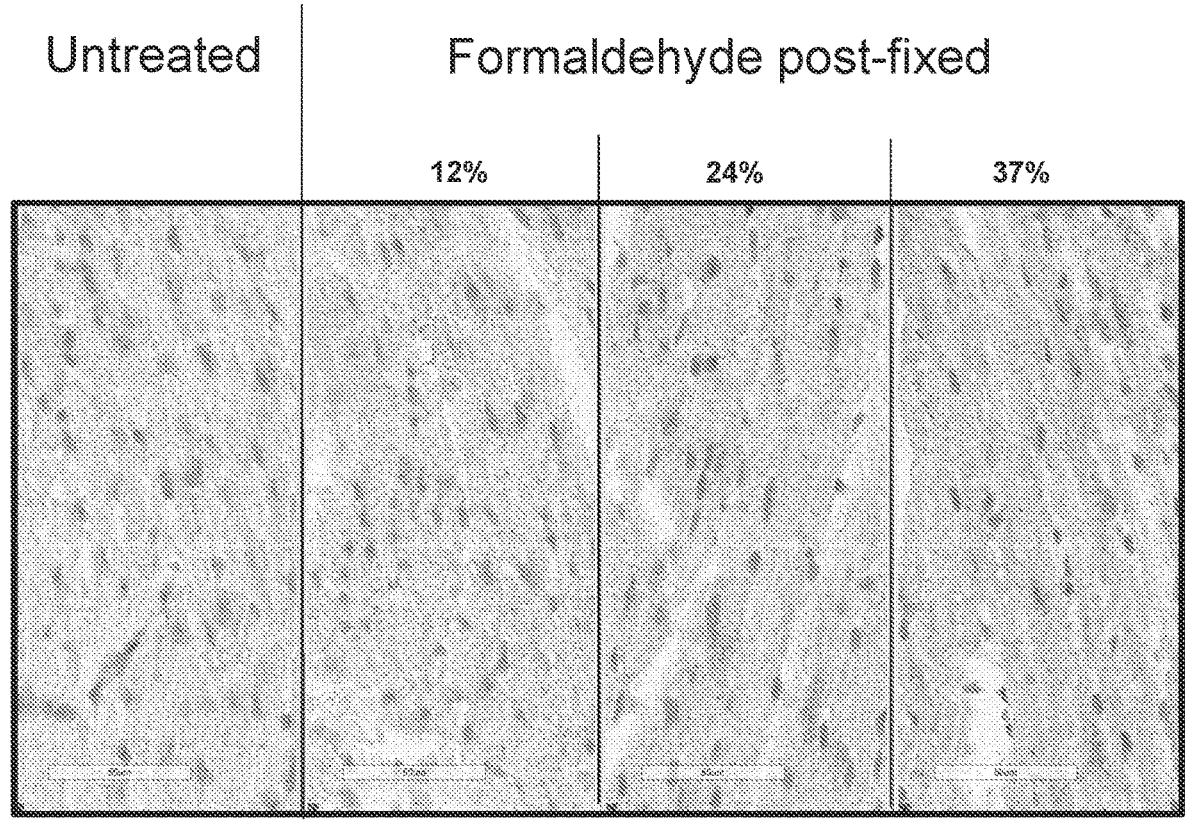
Figure 2B:
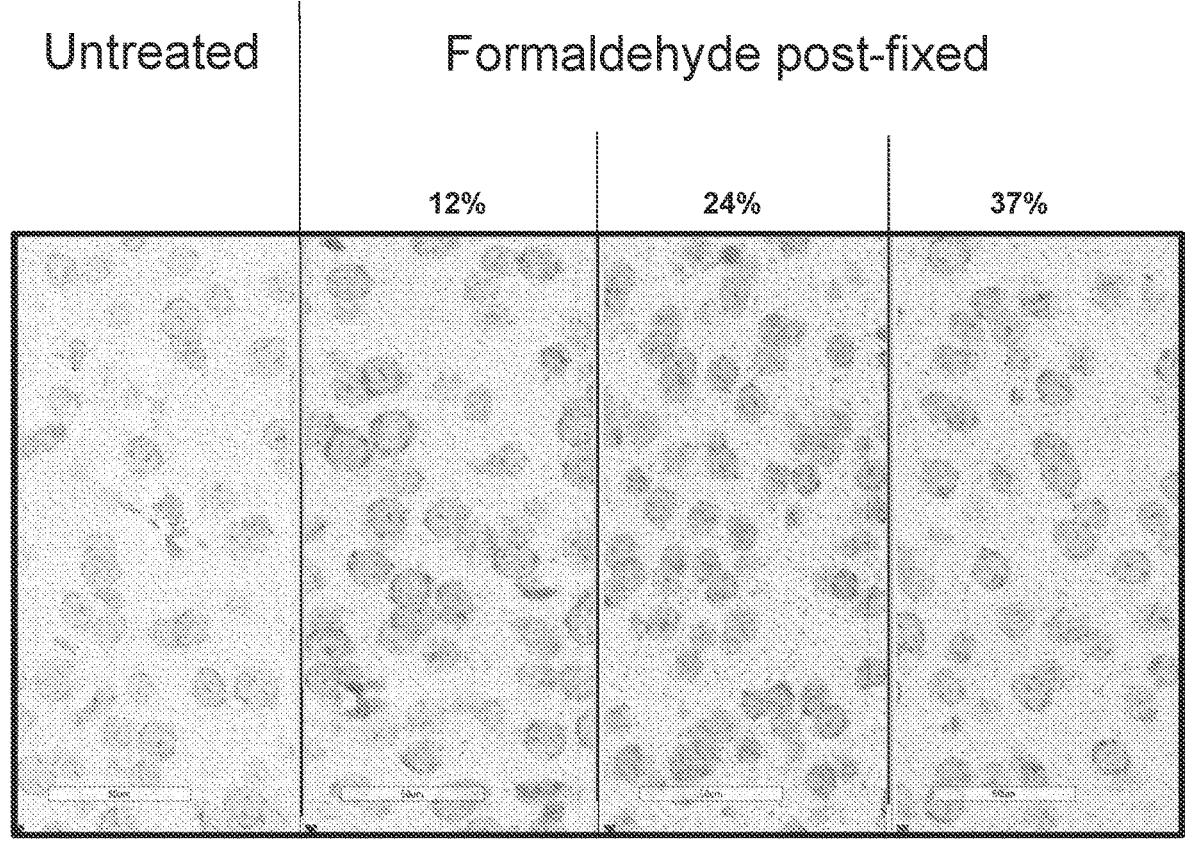

FIGS. 2A-2B show that post-fixation with formaldehyde equal or higher than 12% minimized miRNA loss and improved detection sensitivity by RNAscope® ISH. Mouse formalin-fixed paraffin embedded tissue sections were untreated or post-fixed with a range of formaldehyde concentrations from 12% to 37%. Two types of miRNA were detected using the RNAscope® 2.5 High Definition (HD)-Red Assay following established conditions for formalin-fixed paraffin embedded tissue processing. ISH signal appears as punctate dots and hematoxylin stains individual nuclei. FIG. 2A illustrates the detection of heart-enriched miR-1a-3p following post-fixation process. FIG. 2B illustrates the detection of brain-enriched miR-132-3p.

Figure 3A:
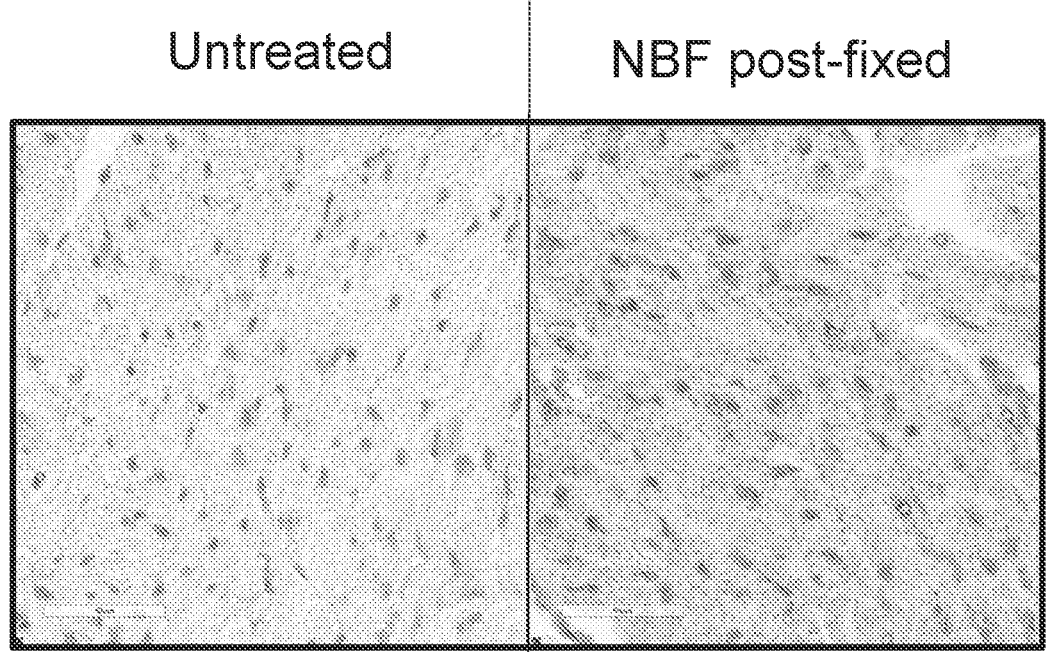
Figure 3B:
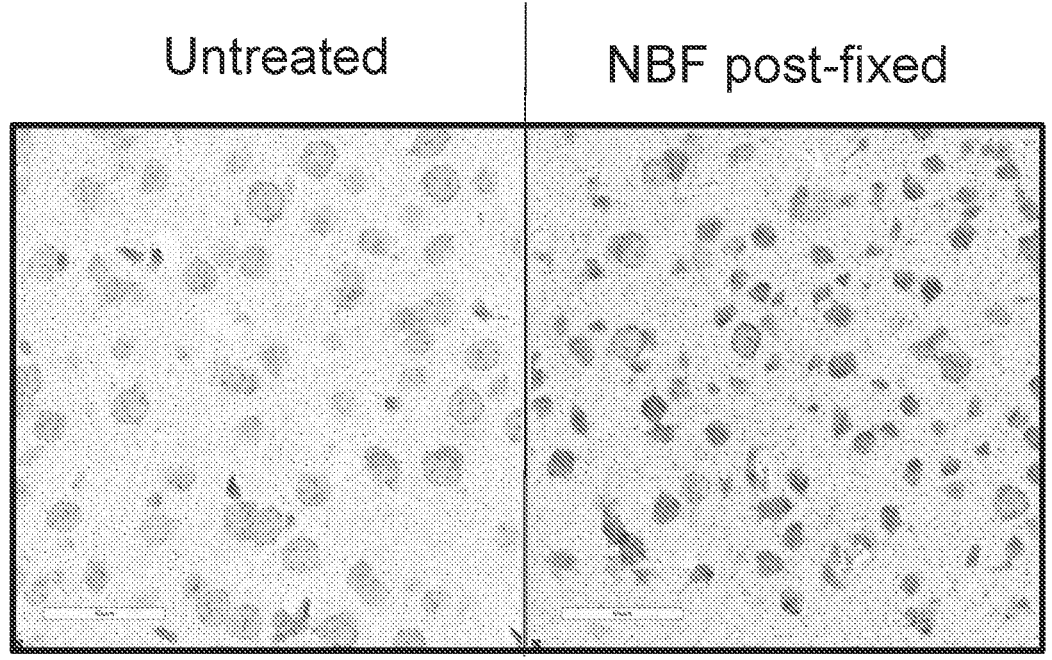
Figure 3C:
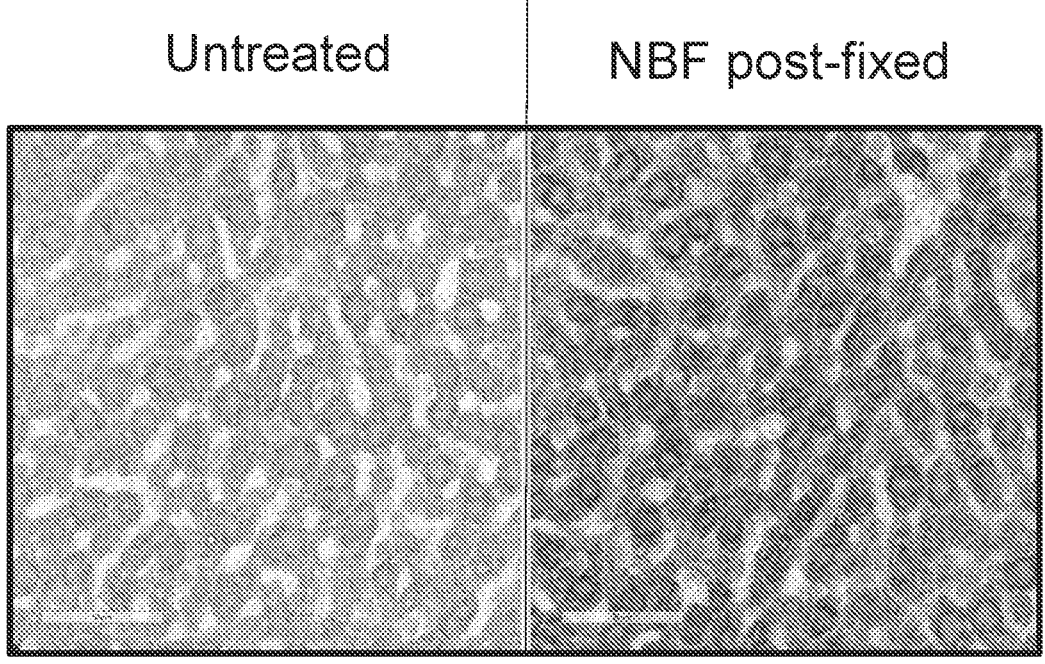
Figure 3D:
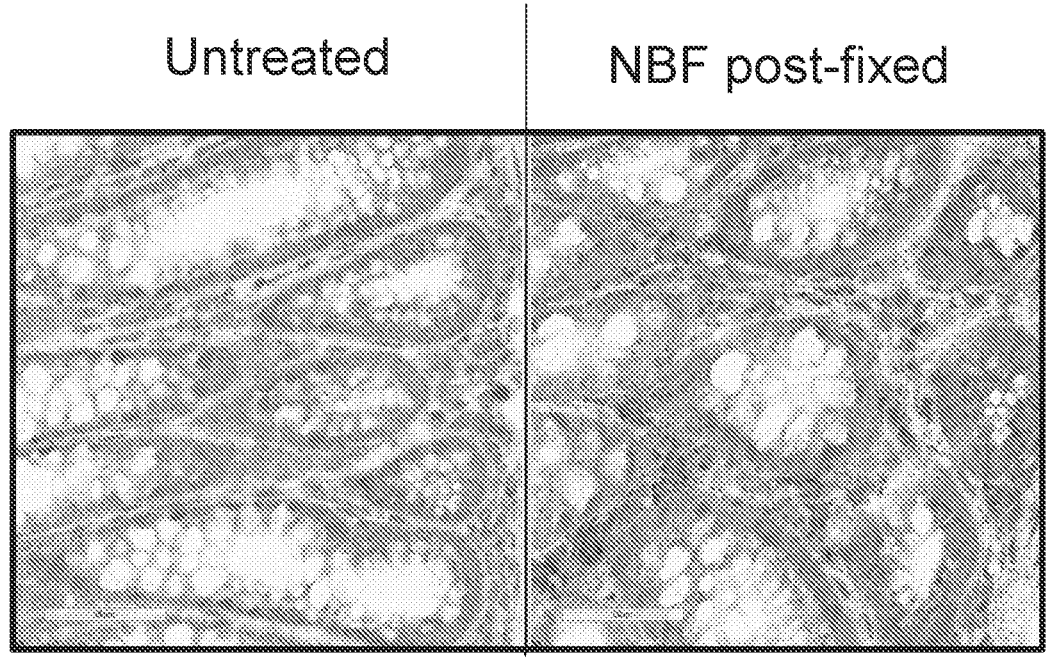

FIGS. 3A-3D show that post-fixation with 10% neutral buffered formalin (NBF), with approximately 4% formaldehyde content, minimized miRNA loss and improved detection sensitivity by RNAscope® ISH. Mouse formalin-fixed paraffin embedded tissue sections were untreated or post-fixed with 10% NBF. Several types of miRNA were detected using the RNAscope® 2.5 High Definition (HD)-Red Assay following established conditions for formalin-fixed paraffin embedded tissue processing. ISH signal appears as punctate dots and hematoxylin stains individual nuclei. FIG. 3A illustrates the detection of heart-enriched miR-1a-3p following post-fixation process. FIG. 3B illustrates the detection of brain-enriched miR-132-3p following post-fixation process. FIG. 3C illustrates the detection of liver-enriched miR-122-5p following post-fixation process. FIG. 3D illustrates the detection of ubiquitously expressed let-7 following post-fixation process.

Figure 4A:
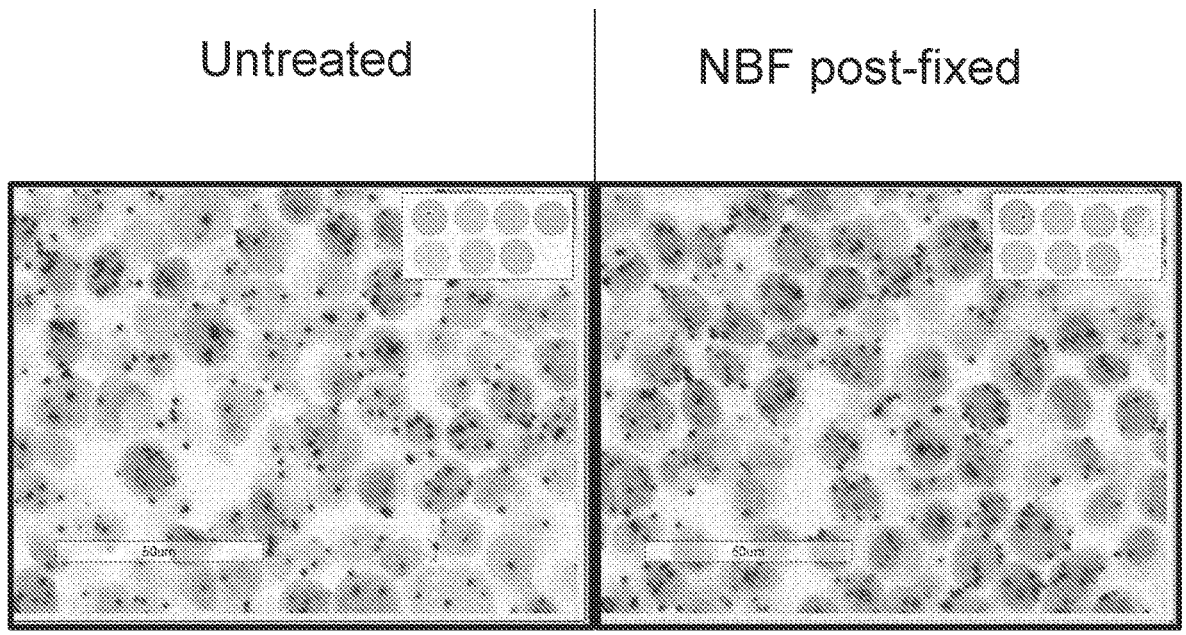
Figure 4B:
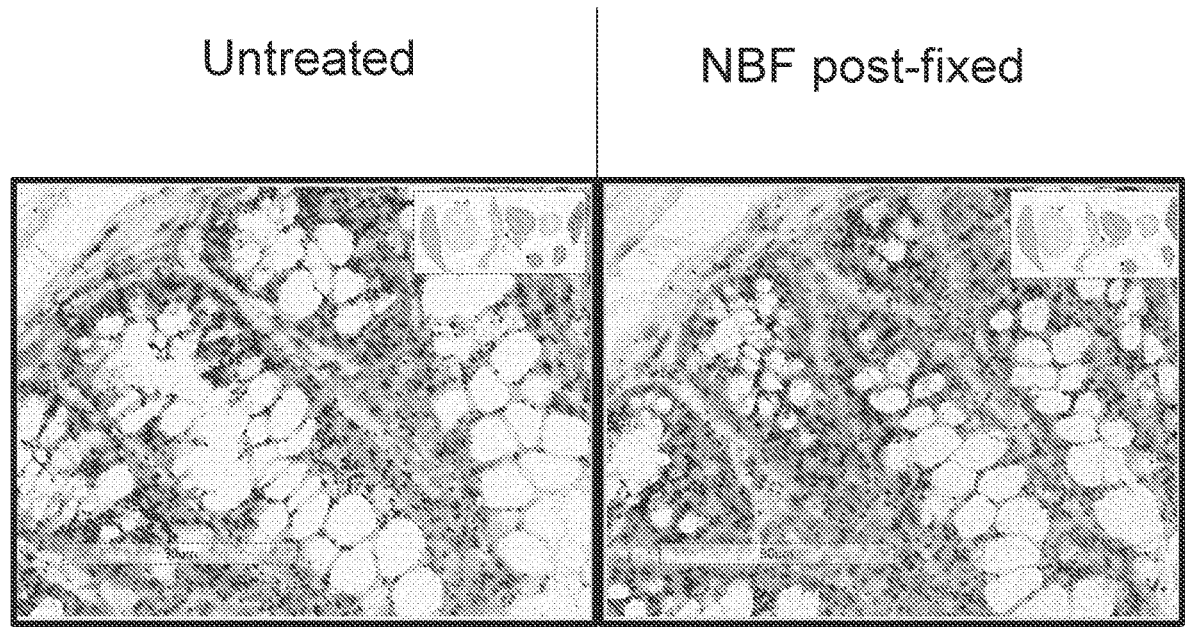
Figure 4C:
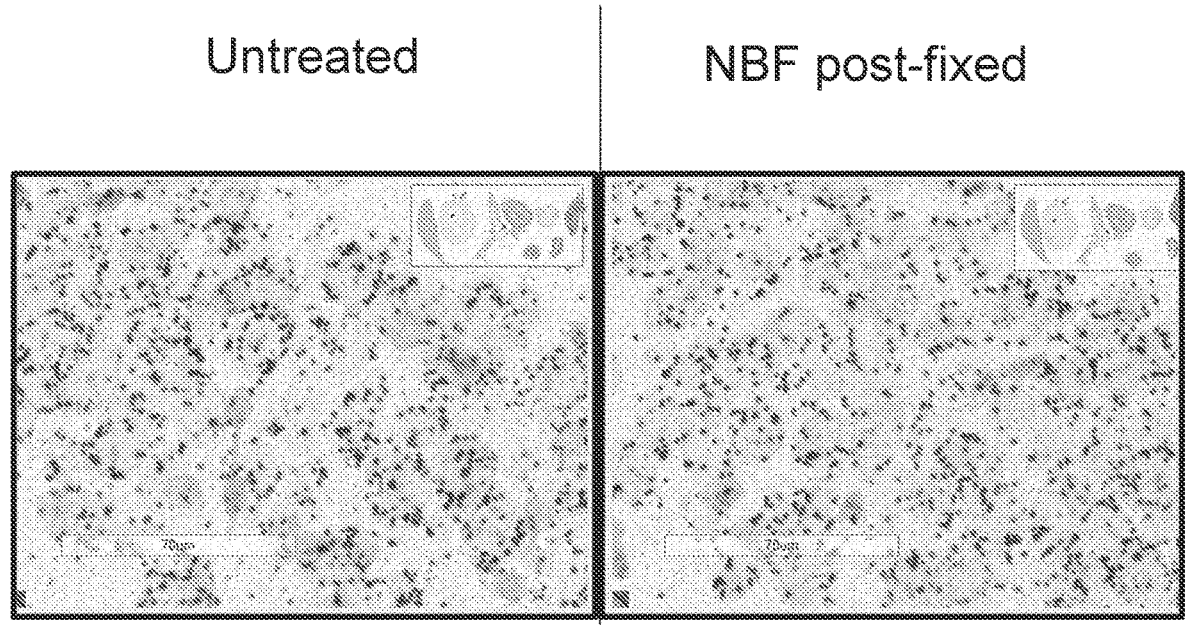

FIGS. 4A-4C show that post-fixation workflow was fully compatible with detection of long RNA species. Human and mouse formalin-fixed paraffin embedded tissues were untreated or post-fixed with 10% NBF and continued with the universal ISH workflow as outlined in FIG. 1. FIG. 4A illustrates human TATA-box-binding protein (TBP) mRNA was detected in human skin A431 cells using the RNAscope® 2.5 High Definition (HD)-Red Assay. FIGS. 4B and 4C show detection of mouse polymerase RNA II polypeptide A (POLR2A) mRNA in mouse intestine samples (FIG. 4B) and in brain tissue (FIG. 4C), respectively.

5. DETAILED DESCRIPTION

The methods provided herein are based, in part, on the unexpected discovery that a post-fixation step after the first fixation step but prior to in situ hybridization resulted in a better retention of small target nucleic acid, e.g., small RNA species in the biological samples and an improved detection sensitivity of the target nucleic acid, e.g., small RNA species, with full compatibility of long nucleic acid species, e.g., long RNA species. The methods provided herein preserve small nucleic acid molecules within their native tissue microenvironment and provide greater detection sensitivity. To minimize loss, previously fixed biological specimens are post-fixed with an aldehyde-containing fixative before processing samples for ISH assay (see FIG. 1), thereby ensuring small nucleic acid preservation within the biological sample. This practical and reliable strategy is fully compatible with standard ISH assays (see FIGS. 2, 3, and 4) and results in enhanced detection sensitivity for small nucleic acids, enabling spatial resolution of target nucleic acids such as sncRNAs, miRNAs, siRNAs, piRNAs, and ASOs.

5.1 Definitions

As used herein, the term "fixation" or "fixing" when made in reference to fixing a biological sample in the in situ hybridization process refers to a procedure to preserve a biological sample from decay due to, e.g., autolysis or putrefaction. It terminates any ongoing biochemical reactions and may also increase the treated tissues' mechanical strength or stability.

As used herein, the term "one or more" refers to, for example, 1 or more, 2 or more, 3 or more, 4 or more, 5 or more, 6 or more, 7 or more, 8 or more, 9 or more, 10 or more, 20 or more, 30 or more, 40 or more, 50 or more, or a greater number, if desired for a particular use.

The terms "detecting" as used herein generally refer to any form of measurement, and include determining whether an element is present or not. This term includes quantitative and/or qualitative determinations.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., fewer than about 3 bases) of mismatch, insertion, or deleted sequence may be present.

The term "sample" as used herein relates to a material or mixture of materials containing one or more components of interest. The term "sample" includes "biological sample" which refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, cells, and exosomes isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

The term "probe" as used herein refers to a capture agent that is directed to a specific target mRNA sequence. Accordingly, each probe of a probe set has a respective target mRNA sequence. In some embodiments, the probe provided herein is a "nucleic acid probe" or "oligonucleotide probe" which refers to a nucleic acid capable of binding to a target nucleic acid of complementary sequence, such as the mRNA biomarkers provided herein, usually through complementary base pairing by forming hydrogen bond. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. The probes can be directly or indirectly labeled with tags, for example, chromophores, lumiphores, or chromogens. By assaying for the presence or absence of the probe, one can detect the presence or absence of a target mRNA biomarker of interest.

As used herein, the term "antisense oligonucleotides (ASO) molecules" or "ASO" refers to short, single-stranded molecules that interact with messenger RNAs to prevent translation of targeted genes.

As used herein, the term "endogenous" refers to the substances originating from within an organism. As used herein, the term "exogenous" refers to the substances originating from outside an organism.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2 Post-Fixation for In Situ Hybridization

Fixation is widely used to preserve a biological sample from decay due to, e.g., autolysis or putrefaction. It terminates any ongoing biochemical reactions and may also increase the treated tissues' mechanical strength or stability. However, it has been known for many years that standard fixation steps often compromise the quality of nucleic acids, DNAs or RNAs, in the biological samples. With the increasing use of molecular testing in the clinical arena, this limitation can unnecessarily restrict the use of these tests. Thus, in this respect, the detection of DNAs and RNAs in histology requires optimization.

Attempts at cataloging RNA species, especially small RNAs, have heavily relied on microarray, quantitative polymerase chain reaction (qPCR), and sequencing approaches. While these methods deliver bulk expression levels, detailed spatial expression information associated with a specific miRNA is lost in the process. This emphasizes the need to detect and catalog miRNAs based on tissue or cell-type specific expression manner. A commonly employed method for visualizing the expression of a gene of interest within the microenvironment of a cell is in situ hybridization (ISH). While many ISH methods are available for detecting messenger RNAs (mRNAs), the detection of small nucleic acids remains problematic to reproducibly detect and quantify their expression.

Traditional tissue fixation methods employing 10% formalin result in optimal preservation of long nucleic acid species, such as mRNAs, but are insufficient for fixing small nucleic acid species such as miRNA, siRNA, piRNA, and ASOs. Recently, a fixation approach was introduced to prevent the loss of miRNAs from histological samples utilizing the cross-linking agent formaldehyde followed by the chemical fixative 1-ethyl-3-(3-dimethylaminopropyl) carbodiimide (EDC), resulting in the retention of miRNAs within the tissue microenvironment as visualized by hapten-labeled probes and colorimetric antibody-based RNA ISH (Pena et al., Nature Methods, 6(2), 139-141, 2010). While useful, this strategy presents a number of challenges. First, the process of cross-liking with EDC is exceptionally sensitive to pH, thereby producing various miRNA retention profiles, which increases the potential variability from assay to assay. Second, due to the instability of the reagent, EDC is formulated fresh and mixed with a stabilizing agent to preserve its fixative properties (Renwick, et al., The Journal of Clinical Investigation, 123(6), 2694-2702, 2013). Therefore, these limitations prevent the practical application of these methods for detecting small RNA species, especially for larger-scale projects. Therefore, a more practical and stable method to minimize loss and improve small nucleic acid detection sensitivity during an ISH assay is required.

Accordingly, embodiments of the present disclosure include a universal and reliable method for preserving small nucleic acid molecules within a biological sample that is fully compatible with established ISH assays. Retention of nucleic acid species is achieved by exposing a previously fixed biological sample to an aldehyde-containing fixative prior to ISH. This strategy eliminates the need to formulate unstable chemical compounds and provides a reliable approach for retaining nucleic acids within tissues leading to enhanced detection sensitivity.

The methods of the present disclosure comprise applying an aldehyde-containing fixative to a previously fixed sample. In some embodiments, provided herein is a method of preserving a target nucleic acid in a previously fixed sample for in situ detection of the target nucleic acid, comprising applying an aldehyde-containing fixative to the sample before conducting in situ hybridization detection assay with a set of one or more probes hybridizing to the target nucleic acid.

In some embodiments, the sample was previously fixed by a chemical fixation with fixative(s). In some embodiments, the sample was previously fixed by immersing the biological sample in the fixative(s), by perfusing the biological sample with the fixative(s), or by applying the fixative(s) in the vapor form to the biological sample. In other embodiments, the sample was previously fixed by physical fixation, for example by heating, exposure to microwaves, cryo-preservation or freeze-drying.

In some embodiments, the sample was previously fixed with coagulant fixative(s). In other embodiments, the sample was previously fixed with non-coagulant fixative(s). In some embodiments, the sample was previously fixed with fixative(s) with denaturation property that remove water from the biological sample. In other embodiments, the sample was previously fixed with fixative(s) that are cross-linking to form chemical bonds between molecules of the biological sample. In some embodiments, the sample was previously fixed with fixative(s) that are additive (i.e., the fixative(s) become part of the biological sample to be processed in the following steps of the histological protocols). In other embodiments, the sample was previously fixed with fixative(s) that are non-additive (i.e., once finish performing the fixation, the fixative(s) will be removed from the biological sample in later steps of the histology protocols).

In one embodiment, the sample was previously fixed with ethanol. In one embodiment, the sample was previously fixed with methanol. In one embodiment, the sample was previously fixed with acetone. In one embodiment, the sample was previously fixed with acetic acid. In one embodiment, the sample was previously fixed with zinc chloride. In one embodiment, the sample was previously fixed with zinc sulfate. In one embodiment, the sample was previously fixed with picric acid. In one embodiment, the sample was previously fixed with formaldehyde. In one embodiment, the sample was previously fixed with glutaraldehyde. In one embodiment, the sample was previously fixed with osmium tetroxide. In some specific embodiments, the sample was previously fixed with carbodiimides. In some specific embodiments, the sample was previously fixed with diimidoesters. In one embodiment, the sample was previously fixed with chloro-s-triazides (cyanuric chloride). In some specific embodiments, the sample was previously fixed with diisocyanates. In one embodiment, the sample was previously fixed with diethylpyrocarbonate (DPC). In some specific embodiments, the sample was previously fixed with maleimides. In one embodiment, the sample was previously fixed with benzoquinone. In one embodiment, the sample was previously fixed with mercuric chloride. In one embodiment, the sample was previously fixed with potassium dichromate. In one embodiment, the sample was previously fixed with potassium permanganate. In one embodiment, the sample was previously fixed with chromic acid.

In one embodiment, the sample was previously fixed with Bouin's fixative, which is a solution of picric acid, formaldehyde, and acetic acid. In one embodiment, the sample was previously fixed with Clarke's fixative, which is a solution of ethanol and acetic acid. In one embodiment, the sample was previously fixed with Carnoy's fixative, which is a solution of ethanol, chloroform, and acetic acid. In one embodiment, the sample was previously fixed with a mixture solution of formaldehyde and glutaraldehyde. In one embodiment, the sample was previously fixed with FAA, which is a solution of ethanol, acetic acid, and formaldehyde. In one embodiment, the sample was previously fixed with periodate-lysine-paraformaldehyde (PLP), which is a solution of paraformaldehyde, L-lysine, and $INaO_4$. In one embodiment, the sample was previously fixed with phosphate buffered formalin (PBF). In one embodiment, the sample was previously fixed with formal calcium, which is a solution of formaldehyde and calcium chloride. In one embodiment, the sample was previously fixed with formal saline, which is a solution of formaldehyde and sodium chloride. In one embodiment, the sample was previously fixed with zinc formalin, which is a solution of formaldehyde and zinc sulphate. In one embodiment, the sample was previously fixed with Zenker's fixative, which is a solution of mercuric chloride, potassium dichromate, and glacial acetic acid. In one embodiment, the sample was previously fixed with Helly's fixative, which is a solution of formaldehyde, potassium dichromate, sodium sulphate, and mercuric chloride. In one embodiment, the sample was previously fixed with B-5 fixative, c mercuric chloride and sodium acetate. In one embodiment, the sample was previously fixed with Hollande's fixative, which is a solution of formaldehyde, copper acetate, picric acid, and acetic acid. In one embodiment, the sample was previously fixed with Gendre's solution, which is a solution of formaldehyde, ethanol, picric acid, and acetic acid glacial. In one embodiment, the sample was previously fixed with Methacarn's fixative, which is a solution of methanol, chloroform, and acetic acid glacial. In one embodiment, the sample was previously fixed with alcoholic formalin, which is a solution of formaldehyde, ethanol, and calcium acetate. In one embodiment, the sample was previously fixed with formol acetic alcohol, which is a solution of formaldehyde, acetic acid glacial, and ethanol.

In some embodiments, the sample was previously fixed with a mixture solution of two, three, four, five, or more fixatives, selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid.

In some embodiments, the sample was previously fixed with two or more fixatives applied not at the same time but consecutively, wherein the two or more fixatives are selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid.

In some embodiments, the sample was previously fixed with fixative(s) that is suitable for preserving nucleic acids. In one embodiment, the fixative is FineFix (see Kothmaier et al., Arch. Pathol. Lab. Med. 135:744-752, 2011). In one embodiment, the fixative is Glyo-fix (see Lykidis et al., Nucleic Acids Res. 35:e85, 2007). In one embodiment, the fixative is Histochoice (see Vince et al., Anal. Cell. Pathol. 15:119-129, 1997). In one embodiment, the fixative is HOPE (see Kothmaier et al., Arch. Pathol. Lab. Med. 135:744-752, 2011). In one embodiment, the fixative is Neo-Fix (see Paavilainen et al., Histochem. Cytochem.: Official J. Histochem. Soc. 58:237-246, 2010). In one embodiment, the fixative is the PAXgene Tissue System (see Nietner et al., Int. J. Pathol. 461:259-269, 2012). In one embodiment, the fixative is RCL2 (see van Essen et al., Clin. Pathol. 63:1090-1094, 2010). In one embodiment, the fixative is Streck's Tissue Fixative (see Burns et al., Histochem. Cytochem. 57:257-264, 2009). In one embodiment, the fixative is UMFIX (see Nadji et al., Appl. Immunohistochem. Mol. Morphol. 13:277-282, 2005). In one embodiment, the fixative is Z7 (see Lykidis et al., Nucleic Acids Res. 35:e85, 2007). In one embodiment, the fixative is ZBF (see Paavilainen et al., Histochem. Cytochem.: Official J. Histochem. Soc. 58:237-246, 2010).

The method for preparing a biological sample for in situ hybridization provided herein comprises applying an aldehyde-containing fixative(s) to previously fixed sample prior to in situ hybridization. In one embodiment, the aldehyde-containing fixative comprises formaldehyde. In one embodiment, the aldehyde-containing fixative comprises glutaraldehyde. In one embodiment, the aldehyde-containing fixative comprises Bouin's fixative, which is a solution of picric acid, formaldehyde, and acetic acid. In one embodiment, the aldehyde-containing fixative comprises a mixture of formaldehyde and glutaraldehyde. In one embodiment, the aldehyde-containing fixative comprises FAA, which is a solution of ethanol, acetic acid, and formaldehyde. In one embodiment, the aldehyde-containing fixative comprises periodate-lysine-paraformaldehyde (PLP), which is a solution of paraformaldehyde, L-lysine, and $INaO_4$. In one embodiment, the aldehyde-containing fixative comprises phosphate buffered formalin (PBF). In one embodiment, the aldehyde-containing fixative comprises formal calcium, which is a solution of formaldehyde and calcium chloride. In one embodiment, the aldehyde-containing fixative comprises formal saline, which is a solution of formaldehyde and sodium chloride. In one embodiment, the aldehyde-containing fixative comprises zinc formalin, which is a solution of formaldehyde and zinc sulphate. In one embodiment, the aldehyde-containing fixative comprises Helly's fixative, which is a solution of formaldehyde, potassium dichromate, sodium sulphate, and mercuric chloride. In one embodiment, the aldehyde-containing fixative comprises Hollande's fixative, which is a solution of formaldehyde, copper acetate, picric acid, and acetic acid. In one embodiment, the aldehyde-containing fixative comprises Gendre's solution, which is a solution of formaldehyde, ethanol, picric acid, and acetic acid glacial. In one embodiment, the aldehyde-containing fixative comprises alcoholic formalin, which is a solution of formaldehyde, ethanol, and calcium acetate. In one embodiment, the aldehyde-containing fixative comprises formol acetic alcohol, which is a solution of formaldehyde, acetic acid glacial, and ethanol. In one embodiment, the aldehyde-containing fixative comprises a mixture of fixatives, wherein at least one fixative of the mixture is formaldehyde or glutaraldehyde. In one embodiment, the aldehyde-containing fixative comprises fixatives that are not used at the same time but consecutively, wherein at least one fixative is formaldehyde or glutaraldehyde.

In some embodiments, the aldehyde-containing fixative comprises about 5% to about 50% formaldehyde. In some embodiments, the aldehyde-containing fixative comprises about 10% to about 40% formaldehyde. In some embodiments, the aldehyde-containing fixative comprises about 12% to about 37% formaldehyde.

In some embodiments, the aldehyde-containing fixative comprises about 5% formaldehyde. In some embodiments, the aldehyde-containing fixative comprises about 6% formaldehyde. In some embodiments, the aldehyde-containing fixative comprises about 7% formaldehyde. In some embodiments, the aldehyde-containing fixative comprises about 8% formaldehyde. In some embodiments, the aldehyde-containing fixative comprises about 9% formaldehyde. In some embodiments, the aldehyde-containing fixative comprises about 10% formaldehyde. In some embodiments, the aldehyde-containing fixative comprises about 11% formaldehyde. In some embodiments, the aldehyde-containing fixative comprises about 12% formaldehyde. In some embodiments, the aldehyde-containing fixative comprises about 13% formaldehyde. In some embodiments, the aldehyde-containing fixative comprises about 14% formaldehyde. In some embodiments, the aldehyde-containing fixative comprises about 15% formaldehyde. In some embodiments, the aldehyde-containing fixative comprises about 16% formaldehyde. In some embodiments, the aldehyde-containing fixative comprises about 17% formaldehyde. In some embodiments, the aldehyde-containing fixative comprises about 18% formaldehyde. In some embodiments, the aldehyde-containing fixative comprises about 19% formaldehyde. In some embodiments, the aldehyde-containing fixative comprises about 20% formaldehyde. In some embodiments, the aldehyde-containing fixative comprises about 30% formaldehyde. In some embodiments, the aldehyde-containing fixative comprises about 35% formaldehyde. In some embodiments, the aldehyde-containing fixative comprises about 40% formaldehyde. In some embodiments, the aldehyde-containing fixative comprises about 50% formaldehyde.

In some embodiments, the sample is treated with the aldehyde-containing fixative for about 2 to about 30 hours. In some embodiments, the sample is treated with the aldehyde-containing fixative for about 2 to about 25 hours. In some embodiments, the sample is treated with the aldehyde-containing fixative for about 2 to about 20 hours. In some embodiments, the sample is treated with the aldehyde-containing fixative for about 2 to about 18 hours. In some embodiments, the sample is treated with the aldehyde-containing fixative for about 2 to about 15 hours. In some embodiments, the sample is treated with the aldehyde-containing fixative for about 2 to about 10 hours. In some embodiments, the sample is treated with the aldehyde-containing fixative for about 2 to about 5 hours. In some embodiments, the sample is treated with the aldehyde-containing fixative for about 2 hours. In some embodiments, the sample is treated with the aldehyde-containing fixative for about 3 hours. In some embodiments, the sample is treated with the aldehyde-containing fixative for about 4 hours. In some embodiments, the sample is treated with the aldehyde-containing fixative for about 5 hours. In some embodiments, the sample is treated with the aldehyde-containing fixative for about 6 hours. In some embodiments, the sample is treated with the aldehyde-containing fixative for about 7 hours. In some embodiments, the sample is treated with the aldehyde-containing fixative for about 8 hours. In some embodiments, the sample is treated with the aldehyde-containing fixative for about 9 hours. In some embodiments, the sample is treated with the aldehyde-containing fixative for about 10 hours. In some embodiments, the sample is treated with the aldehyde-containing fixative for about 11 hours. In some embodiments, the sample is treated with the aldehyde-containing fixative for about 12 hours. In some embodiments, the sample is treated with the aldehyde-containing fixative for about 13 hours. In some embodiments, the sample is treated with the aldehyde-containing fixative for about 14 hours. In some embodiments, the sample is treated with the aldehyde-containing fixative for about 15 hours. In some embodiments, the sample is treated with the aldehyde-containing fixative for about 16 hours. In some embodiments, the sample is treated with the aldehyde-containing fixative for about 17 hours. In some embodiments, the sample is treated with the aldehyde-containing fixative for about 18 hours. In some embodiments, the sample is treated with the aldehyde-containing fixative for about 19 hours. In some embodiments, the sample is treated with the aldehyde-containing fixative for about 20 hours.

In some embodiments, the sample is treated with formaldehyde for about 2 to about 30 hours. In some embodiments, the sample is treated with formaldehyde for about 2 to about 25 hours. In some embodiments, the sample is treated with formaldehyde for about 2 to about 20 hours. In some embodiments, the sample is treated with formaldehyde for about 2 to about 18 hours. In some embodiments, the sample is treated with formaldehyde for about 2 to about 15 hours. In some embodiments, the sample is treated with formaldehyde for about 2 to about 10 hours. In some embodiments, the sample is treated with formaldehyde for about 2 to about 5 hours. In some embodiments, the sample is treated with formaldehyde for about 2 hours. In some embodiments, the sample is treated with formaldehyde for about 3 hours. In some embodiments, the sample is treated with formaldehyde for about 4 hours. In some embodiments, the sample is treated with formaldehyde for about 5 hours. In some embodiments, the sample is treated with formaldehyde for about 6 hours. In some embodiments, the sample is treated with formaldehyde for about 7 hours. In some embodiments, the sample is treated with formaldehyde for about 8 hours. In some embodiments, the sample is treated with formaldehyde for about 9 hours. In some embodiments, the sample is treated with formaldehyde for about 10 hours. In some embodiments, the sample is treated with formaldehyde for about 11 hours. In some embodiments, the sample is treated with formaldehyde for about 12 hours. In some embodiments, the sample is treated with formaldehyde for about 13 hours. In some embodiments, the sample is treated with formaldehyde for about 14 hours. In some embodiments, the sample is treated with formaldehyde for about 15 hours. In some embodiments, the sample is treated with formaldehyde for about 16 hours. In some embodiments, the sample is treated with formaldehyde for about 17 hours. In some embodiments, the sample is treated with formaldehyde for about 18 hours. In some embodiments, the sample is treated with formaldehyde for about 19 hours. In some embodiments, the sample is treated with formaldehyde for about 20 hours.

In some specific embodiments, the sample is treated with an aldehyde-containing fixative comprising less than about 12% formaldehyde for more than about 15 hours. In some specific embodiments, the sample is treated with an aldehyde-containing fixative comprising less than about 12% formaldehyde for about 18 hours. In some specific embodiments, the sample is treated with an aldehyde-containing fixative comprising less than about 12% formaldehyde for about 19 hours. In some specific embodiments, the sample is treated with an aldehyde-containing fixative comprising less than about 12% formaldehyde for about 20 hours. In some specific embodiments, the sample is treated with an aldehyde-containing fixative comprising less than about 12% formaldehyde for about 25 hours.

In other specific embodiments, the sample is treated with an aldehyde-containing fixative comprising about 12% or more formaldehyde for less than about 10 hours. In other specific embodiments, the sample is treated with an aldehyde-containing fixative comprising about 12% or more formaldehyde for about 10 hours. In other specific embodiments, the sample is treated with an aldehyde-containing fixative comprising about 12% or more formaldehyde for about 9 hours. In other specific embodiments, the sample is treated with an aldehyde-containing fixative comprising about 12% or more formaldehyde for about 8 hours. In other specific embodiments, the sample is treated with an aldehyde-containing fixative comprising about 12% or more formaldehyde for about 7 hours. In other specific embodiments, the sample is treated with an aldehyde-containing fixative comprising about 12% or more formaldehyde for about 6 hours. In other specific embodiments, the sample is treated with an aldehyde-containing fixative comprising about 12% or more formaldehyde for about 5 hours. In other specific embodiments, the sample is treated with an aldehyde-containing fixative comprising about 12% or more formaldehyde for about 4 hours. In other specific embodiments, the sample is treated with an aldehyde-containing fixative comprising about 12% or more formaldehyde for about 3 hours. In other specific embodiments, the sample is treated with an aldehyde-containing fixative comprising about 12% or more formaldehyde for about 2 hours.

In some specific embodiments, the aldehyde-containing fixative is in a buffer with a pH of about 6. In some specific embodiments, the aldehyde-containing fixative is in a buffer with a pH of about 6.5. In some specific embodiments, the aldehyde-containing fixative is in a buffer with a pH of about 7. In some specific embodiments, the aldehyde-containing fixative is in a buffer with a pH of about 7.5. In some specific embodiments, the aldehyde-containing fixative is in a buffer with a pH of about 8. In some specific embodiments, the aldehyde-containing fixative is in a buffer with a pH of about 8.5. In some specific embodiments, the aldehyde-containing fixative is in a buffer with a pH of about 9.

In some embodiments, the fixation is carried out at a temperature of about 4-50° C. In some embodiments, the fixation is carried out at a temperature of about 4° C. In some embodiments, the fixation is carried out at a temperature of about 10° C. In some embodiments, the fixation is carried out at a temperature of about 20° C. In some embodiments, the fixation is carried out at a temperature of about 25° C. In some embodiments, the fixation is carried out at a temperature of about 30° C. In some embodiments, the fixation is carried out at a temperature of about 40° C. In some embodiments, the fixation is carried out at a temperature of about 50° C. In some embodiments, the fixation is carried out at ambient temperature.

In certain embodiments, the method provided herein comprises treating a previously fixed sample with an aldehyde-containing fixative, wherein the aldehyde-containing fixative is in an isotonic buffer with a pH at about 6 and its aldehyde percentage being equal or higher than about 12%, and wherein the fixation is carried out at a temperature of about 4° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 7 and its aldehyde percentage being equal or higher than about 12%, and wherein the fixation is carried out at a temperature of about 4° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hour. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 8 and its aldehyde percentage being equal or higher than about 12%, and wherein the fixation is carried out at a temperature of about 4° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 6 and its aldehyde percentage being equal or higher than about 12%, and wherein the fixation is carried out at ambient temperature. In one embodiment, the fixation lasts for about 1 hour.

In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 7 and its aldehyde percentage being equal or higher than about 12%, and wherein the fixation is carried out at ambient temperature. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 8 and its aldehyde percentage being equal or higher than about 12%, and wherein the fixation is carried out at ambient temperature. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 6 and its aldehyde percentage being equal or higher than about 12%, and wherein the fixation is carried out at a temperature of about 50° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 7 and its aldehyde percentage being equal or higher than about 12%, and wherein the fixation is carried out at a temperature of about 50° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an aldehyde-containing fixative, wherein the aldehyde-containing fixative is in an isotonic buffer with a pH at about 8 and its aldehyde percentage being equal or higher than about 12%, and wherein the fixation is carried out at a temperature of about 50° C. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours. In one embodiment, the fixation lasts for about 4 hours.

In certain embodiments, the method provided herein comprises treating a previously fixed sample with an alde-hyde-containing fixative, wherein the aldehyde-containing fixative is in an isotonic buffer with a pH at about 6 and its aldehyde percentage being less than about 12%, and wherein the fixation is carried out at a temperature of about 4° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an alde-hyde-containing fixative, wherein the aldehyde-containing fixative is in an isotonic buffer with a pH at about 7 and its aldehyde percentage being less than about 12%, and wherein the fixation is carried out at a temperature of about 4° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an alde-hyde-containing fixative, wherein the aldehyde-containing fixative is in an isotonic buffer with a pH at about 8 and its aldehyde percentage being less than about 12%, and wherein the fixation is carried out at a temperature of about 4° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an alde-hyde-containing fixative, wherein the aldehyde-containing fixative is in an isotonic buffer with a pH at about 6 and its aldehyde percentage being less than about 12%, and wherein the fixation is carried out at ambient temperature. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an alde-hyde-containing fixative, wherein the aldehyde-containing fixative is in an isotonic buffer with a pH at about 7 and its aldehyde percentage being less than about 12%, and wherein the fixation is carried out at ambient temperature. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an aldehyde-containing fixative, wherein the aldehyde-containing fixative is in an isotonic buffer with a pH at about 8 and its aldehyde percentage being less than about 12%, and wherein the fixation is carried out at ambient temperature. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an aldehyde-containing fixative, wherein the aldehyde-containing fixative is in an isotonic buffer with a pH at about 6 and its aldehyde percentage being less than about 12%, and wherein the fixation is carried out at a temperature of about 50° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an aldehyde-containing fixative, wherein the aldehyde-containing fixative is in an isotonic buffer with a pH at about 7 and its aldehyde percentage being less than about 12%, and wherein the fixation is carried out at a temperature of about 50° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with an aldehyde-containing fixative, wherein the aldehyde-containing fixative is in an isotonic buffer with a pH at about 8 and its aldehyde percentage being less than about 12%, and wherein the fixation is carried out at a temperature of about 50° C. In one embodiment, the fixation lasts for about 2 hours. In one embodiment, the fixation lasts for about 3 hours. In one embodiment, the fixation lasts for about 4 hours. In one embodiment, the fixation lasts for about 5 hours. In one embodiment, the fixation lasts for about 6 hours. In one embodiment, the fixation lasts for about 7 hours. In one embodiment, the fixation lasts for about 8 hours. In one embodiment, the fixation lasts for about 9 hours. In one embodiment, the fixation lasts for about 10 hours. In one embodiment, the fixation lasts for about 11 hours. In one embodiment, the fixation lasts for about 12 hours. In one embodiment, the fixation lasts for about 13 hours. In one embodiment, the fixation lasts for about 14 hours. In one embodiment, the fixation lasts for about 15 hours. In one embodiment, the fixation lasts for about 16 hours. In one embodiment, the fixation lasts for about 16 hours. In one embodiment, the fixation lasts for about 17 hours. In one embodiment, the fixation lasts for about 18 hours. In one embodiment, the fixation lasts for about 24 hours. In one embodiment, the fixation lasts for about 36 hours. In one embodiment, the fixation lasts for about 48 hours.

In certain embodiments, the method provided herein comprises treating a previously fixed sample with formaldehyde equal or higher than about 12% in an isotonic buffer with a neutral or near neutral pH, and the fixation is carried out at ambient temperature. In one embodiment, the fixation lasts for about 0.5 hour. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours.

In certain embodiments, the method provided herein comprises treating a previously fixed sample with formaldehyde below about 12% in an isotonic buffer with a neutral or near neutral pH, and the fixation is carried out at ambient temperature. In one embodiment, the fixation lasts for about 12 hours. In one embodiment, the fixation lasts for about 14 hours. In one embodiment, the fixation lasts for about 16 hours. In one embodiment, the fixation lasts for about 18 hours. In one embodiment, the fixation lasts for about 20 hours. In one embodiment, the fixation lasts for about 22 hours. In one embodiment, the fixation lasts for about 24 hours.

In certain embodiments, the method provided herein comprises treating a previously fixed sample with about 12% formaldehyde in phosphate buffered saline, and the fixation is carried out at ambient temperature. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours.

In certain embodiments, the method provided herein comprises treating a previously fixed sample with about 24% formaldehyde in phosphate buffered saline, and the fixation is carried out at ambient temperature. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours.

In certain embodiments, the method provided herein comprises treating a previously fixed sample with about 37% formaldehyde in phosphate buffered saline, and the fixation is carried out at ambient temperature. In one embodiment, the fixation lasts for about 1 hour. In one embodiment, the fixation lasts for about 1.5 hours. In one embodiment, the fixation lasts for about 2 hours. In one embodiment, the fixation lasts for about 2.5 hours. In one embodiment, the fixation lasts for about 3 hours. In one embodiment, the fixation lasts for about 3.5 hours.

In certain embodiments, the method provided herein comprises treating a previously fixed sample with about 10% neutral buffered formalin, and the fixation is carried out at ambient temperature. In one embodiment, the fixation lasts for about 12 hours. In one embodiment, the fixation lasts for about 14 hours. In one embodiment, the fixation lasts for about 16 hours. In one embodiment, the fixation lasts for about 18 hours. In one embodiment, the fixation lasts for about 20 hours. In one embodiment, the fixation lasts for about 22 hours. In one embodiment, the fixation lasts for about 24 hours.

In other embodiments, the method provided here is for preparing a biological sample for in situ hybridization comprising a first fixation step comprising fixing the biological sample with an agent; and a post-fixation step after the first fixation step prior to in situ hybridization comprising fixing the biological sample with an aldehyde-containing fixative.

In some embodiments, the first fixation step is a physical fixation. In one embodiment, the first fixation step is heating. In one embodiment, the first fixation step is exposure to microwaves. In one embodiment, the first fixation step is cryo-preservation or freeze-drying. In other embodiments, the first fixation step is a chemical fixation with fixative(s). In some embodiments, the first fixation step is a chemical fixation by immersing the biological sample in the fixative (s). In some embodiments, the first fixation step is a chemical fixation by perfusing the biological sample with the fixative(s). In some embodiments, the first fixation step is a chemical fixation by applying the fixative(s) in the vapor form to the biological sample.

In some embodiments, the first fixation step is a chemical fixation with coagulant fixative(s). In other embodiments, the first fixation step is a chemical fixation with non-coagulant fixative(s). In some embodiments, the first fixation step is a chemical fixation with fixative(s) with denaturation property that remove water from the biological sample. In other embodiments, the first fixation step is a chemical fixation with fixative(s) that are cross-linking to form chemical bonds between molecules of the biological sample. In some embodiments, the first fixation step is a chemical fixation with fixative(s) that are additive (i.e., the fixative(s) become part of the biological sample to be processed in the following steps of the histological protocols). In other embodiments, the first fixation step is a chemical fixation with fixative(s) that are non-additive (i.e., once finish performing the fixation, the fixative(s) will be removed from the biological sample in later steps of the histological protocols).

In one embodiment, the first fixation step is a chemical fixation with ethanol. In one embodiment, the first fixation step is a chemical fixation with methanol. In one embodiment, the first fixation step is a chemical fixation with acetone. In one embodiment, the first fixation step is a chemical fixation with acetic acid. In one embodiment, the first fixation step is a chemical fixation with zinc chloride. In one embodiment, the first fixation step is a chemical fixation with zinc sulfate. In one embodiment, the first fixation step is a chemical fixation with picric acid. In one embodiment, the first fixation step is a chemical fixation with formaldehyde. In one embodiment, the first fixation step is a chemical fixation with glutaraldehyde. In one embodiment, the first fixation step is a chemical fixation with osmium tetroxide. In some specific embodiments, the first fixation step is a chemical fixation with carbodiimides. In some specific embodiments, the first fixation step is a chemical fixation with diimidoesters. In one embodiment, the first fixation step is a chemical fixation with chloro-s-triazides (cyanuric chloride). In some specific embodiments, the first fixation step is a chemical fixation with diisocyanates. In one embodiment, the first fixation step is a chemical fixation with diethylpyrocarbonate (DPC). In some specific embodiments, the first fixation step is a chemical fixation with maleimides. In one embodiment, the first fixation step is a chemical fixation with benzoquinone. In one embodiment, the first fixation step is a chemical fixation with mercuric chloride. In one embodiment, the first fixation step is a chemical fixation with potassium dichromate. In one embodiment, the first fixation step is a chemical fixation with potassium permanganate. In one embodiment, the first fixation step is a chemical fixation with chromic acid.

In one embodiment, the first fixation step is a chemical fixation with Bouin's fixative, which is a solution of picric acid, formaldehyde, and acetic acid. In one embodiment, the first fixation step is a chemical fixation with Clarke's fixative, which is a solution of ethanol and acetic acid. In one embodiment, the first fixation step is a chemical fixation with Carnoy's fixative, which is a solution of ethanol, chloroform, and acetic acid. In one embodiment, the first fixation step is a chemical fixation with a mixture solution of formaldehyde and glutaraldehyde. In one embodiment, the first fixation step is a chemical fixation with FAA, which is a solution of ethanol, acetic acid, and formaldehyde. In one embodiment, the first fixation step is a chemical fixation with periodate-lysine-paraformaldehyde (PLP), which is a solution of paraformaldehyde, L-lysine, and $INaO_4$. In one embodiment, the first fixation step is a chemical fixation with phosphate buffered formalin (PBF). In one embodiment, the first fixation step is a chemical fixation with formal calcium, which is a solution of formaldehyde and calcium chloride. In one embodiment, the first fixation step is a chemical fixation with formal saline, which is a solution of formaldehyde and sodium chloride. In one embodiment, the first fixation step is a chemical fixation with zinc formalin, which is a solution of formaldehyde and zinc sulphate. In one embodiment, the first fixation step is a chemical fixation with Zenker's fixative, which is a solution of mercuric chloride, potassium dichromate, and glacial acetic acid. In one embodiment, the first fixation step is a chemical fixation with Helly's fixative, which is a solution of formaldehyde, potassium dichromate, sodium sulphate, and mercuric chloride. In one embodiment, the first fixation step is a chemical fixation with B-5 fixative, c mercuric chloride and sodium acetate. In one embodiment, the first fixation step is a chemical fixation with Hollande's fixative, which is a solution of formaldehyde, copper acetate, picric acid, and acetic acid. In one embodiment, the first fixation step is a chemical fixation with Gendre's solution, which is a solution of formaldehyde, ethanol, picric acid, and acetic acid glacial. In one embodiment, the first fixation step is a chemical fixation with Methacarn's fixative, which is a solution of methanol, chloroform, and acetic acid glacial. In one embodiment, the first fixation step is a chemical fixation with alcoholic formalin, which is a solution of formaldehyde, ethanol, and calcium acetate. In one embodiment, the first fixation step is a chemical fixation with formol acetic alcohol, which is a solution of formaldehyde, acetic acid glacial, and ethanol.

In some embodiments, the first fixation step is a chemical fixation with a mixture solution of two, three, four, five, or more fixatives, selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid In some embodiments, the first fixation step is a chemical fixation with two or more fixatives applied not at the same time but consecutively, wherein the two or more fixatives are selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid.

In some embodiments, the first fixation step is a chemical fixation with fixative(s) that is suitable for preserving nucleic acids. In one embodiment, the first fixation step is a chemical fixation with FineFix (see Kothmaier et al., Arch. Pathol. Lab. Med. 135:744-752, 2011). In one embodiment, the first fixation step is a chemical fixation with Glyo-fix (see Lykidis et al., Nucleic Acids Res. 35:e85, 2007). In one embodiment, the first fixation step is a chemical fixation with Histochoice (see Vince et al., Anal. Cell. Pathol. 15:119-129, 1997). In one embodiment, the first fixation step is a chemical fixation with HOPE (see Kothmaier et al., Arch. Pathol. Lab. Med. 135:744-752, 2011). In one embodiment, the first fixation step is a chemical fixation with Neo-Fix (see Paavilainen et al., Histochem. Cytochem.: Official J. Histochem. Soc. 58:237-246, 2010). In one embodiment, the first fixation step is a chemical fixation with the PAXgene Tissue System (see Nietner et al., Int. J. Pathol. 461:259-269, 2012). In one embodiment, the first fixation step is a chemical fixation with RCL2 (see van Essen et al., Clin. Pathol. 63:1090-1094, 2010). In one embodiment, the first fixation step is a chemical fixation with Streck's Tissue Fixative (see Burns et al., Histochem. Cytochem. 57:257-264, 2009). In one embodiment, the first fixation step is a chemical fixation with UMFIX (see Nadji et al., Appl. Immunohistochem. Mol. Morphol. 13:277-282, 2005). In one embodiment, the first fixation step is a chemical fixation with Z7 (see Lykidis et al., Nucleic Acids Res. 35:e85, 2007). In one embodiment, the first fixation step is a chemical fixation with ZBF (see Paavilainen et al., Histochem. Cytochem.: Official J. Histochem. Soc. 58:237-246, 2010).

In certain embodiments, the method for preparing a biological sample for in situ hybridization provided herein comprises a post-fixation step with aldehyde-containing fixative(s) after the first fixation step and prior to in situ hybridization. In one embodiment, the post-fixation step is a chemical fixation with formaldehyde. In one embodiment, the post-fixation step is a chemical fixation with glutaraldehyde. In one embodiment, the post-fixation step is a chemical fixation with Bouin's fixative, which is a solution of picric acid, formaldehyde, and acetic acid. In one embodiment, the post-fixation step is a chemical fixation with a mixture of formaldehyde and glutaraldehyde. In one embodiment, the post-fixation step is a chemical fixation with FAA, which is a solution of ethanol, acetic acid, and formaldehyde. In one embodiment, the post-fixation step is a chemical fixation with periodate-lysine-paraformaldehyde (PLP), which is a solution of paraformaldehyde, L-lysine, and $INaO_4$. In one embodiment, the post-fixation step is a chemical fixation with phosphate buffered formalin (PBF). In one embodiment, the post-fixation step is a chemical fixation with formal calcium, which is a solution of formaldehyde and calcium chloride. In one embodiment, the post-fixation step is a chemical fixation with formal saline, which is a solution of formaldehyde and sodium chloride. In one embodiment, the post-fixation step is a chemical fixation with zinc formalin, which is a solution of formaldehyde and zinc sulphate. In one embodiment, the post-fixation step is a chemical fixation with Helly's fixative, which is a solution of formaldehyde, potassium dichromate, sodium sulphate, and mercuric chloride. In one embodiment, the post-fixation step is a chemical fixation with Hollande's fixative, which is a solution of formaldehyde, copper acetate, picric acid, and acetic acid. In one embodiment, the post-fixation step is a chemical fixation with Gendre's solution, which is a solution of formaldehyde, ethanol, picric acid, and acetic acid glacial. In one embodiment, the post-fixation step is a chemical fixation with alcoholic formalin, which is a solution of formaldehyde, ethanol, and calcium acetate. In one embodiment, the post-fixation step is a chemical fixation with formol acetic alcohol, which is a solution of formaldehyde, acetic acid glacial, and ethanol. In one embodiment, the post-fixation step is a chemical fixation with a mixture of fixatives, wherein at least one fixative of the mixture is formaldehyde or glutaraldehyde. In one embodiment, the post-fixation step is a chemical fixation with fixatives that are not used at the same time but consecutively, wherein at least one fixative is formaldehyde or glutaraldehyde.

In some embodiments, the aldehyde-containing fixative comprises formaldehyde. In other embodiments, the aldehyde-containing fixative comprises glutaraldehyde.

In some embodiments, the aldehyde-containing fixative comprises about 5% to about 50% formaldehyde. In some embodiments, the aldehyde-containing fixative comprises about 10% to about 40% formaldehyde. In some embodiments, the aldehyde-containing fixative comprises about 12% to about 37% formaldehyde.

In some embodiments, the aldehyde-containing fixative comprises about 5% formaldehyde. In some embodiments, the aldehyde-containing fixative comprises about 6% formaldehyde. In some embodiments, the aldehyde-containing fixative comprises about 7% formaldehyde. In some embodiments, the aldehyde-containing fixative comprises about 8% formaldehyde. In some embodiments, the aldehyde-containing fixative comprises about 9% formaldehyde. In some embodiments, the aldehyde-containing fixative comprises about 10% formaldehyde. In some embodiments, the aldehyde-containing fixative comprises about 11% formaldehyde. In some embodiments, the aldehyde-containing fixative comprises about 12% formaldehyde. In some embodiments, the aldehyde-containing fixative comprises about 13% formaldehyde. In some embodiments, the aldehyde-containing fixative comprises about 14% formaldehyde. In some embodiments, the aldehyde-containing fixative comprises about 15% formaldehyde. In some embodiments, the aldehyde-containing fixative comprises about 16% formaldehyde. In some embodiments, the aldehyde-containing fixative comprises about 17% formaldehyde. In some embodiments, the aldehyde-containing fixative comprises about 18% formaldehyde. In some embodiments, the aldehyde-containing fixative comprises about 19% formaldehyde. In some embodiments, the aldehyde-containing fixative comprises about 20% formaldehyde. In some embodiments, the aldehyde-containing fixative comprises about 30% formaldehyde. In some embodiments, the aldehyde-containing fixative comprises about 35% formaldehyde. In some embodiments, the aldehyde-containing fixative comprises about 40% formaldehyde. In some embodiments, the aldehyde-containing fixative comprises about 50% formaldehyde.

In some embodiments, in the post-fixation step, the sample is treated with the aldehyde-containing fixative for about 2 to about 30 hours. In some embodiments, in the post-fixation step, the sample is treated with the aldehyde-containing fixative for about 2 to about 25 hours. In some embodiments, in the post-fixation step, the sample is treated with the aldehyde-containing fixative for about 2 to about 20 hours. In some embodiments, in the post-fixation step, the sample is treated with the aldehyde-containing fixative for about 2 to about 18 hours. In some embodiments, in the post-fixation step, the sample is treated with the aldehyde-containing fixative for about 2 to about 15 hours. In some embodiments, in the post-fixation step, the sample is treated with the aldehyde-containing fixative for about 2 to about 10 hours. In some embodiments, in the post-fixation step, the sample is treated with the aldehyde-containing fixative for about 2 to about 5 hours. In some embodiments, in the post-fixation step, the sample is treated with the aldehyde-containing fixative for about 2 hours. In some embodiments, in the post-fixation step, the sample is treated with the aldehyde-containing fixative for about 3 hours. In some embodiments, in the post-fixation step, the sample is treated with the aldehyde-containing fixative for about 4 hours. In some embodiments, in the post-fixation step, the sample is treated with the aldehyde-containing fixative for about 5 hours. In some embodiments, in the post-fixation step, the sample is treated with the aldehyde-containing fixative for about 6 hours. In some embodiments, in the post-fixation step, the sample is treated with the aldehyde-containing fixative for about 7 hours. In some embodiments, in the post-fixation step, the sample is treated with the aldehyde-containing fixative for about 8 hours. In some embodiments, in the post-fixation step, the sample is treated with the aldehyde-containing fixative for about 9 hours. In some embodiments, in the post-fixation step, the sample is treated with the aldehyde-containing fixative for about 10 hours. In some embodiments, in the post-fixation step, the sample is treated with the aldehyde-containing fixative for about 11 hours. In some embodiments, in the post-fixation step, the sample is treated with the aldehyde-containing fixative for about 12 hours. In some embodiments, in the post-fixation step, the sample is treated with the aldehyde-containing fixative for about 13 hours. In some embodiments, in the post-fixation step, the sample is treated with the aldehyde-containing fixative for about 14 hours. n some embodiments, in the post-fixation step, the sample is treated with the aldehyde-containing fixative for about 15 hours. In some embodiments, in the post-fixation step, the sample is treated with the aldehyde-containing fixative for about 16 hours. In some embodiments, in the post-fixation step, the sample is treated with the aldehyde-containing fixative for about 17 hours. In some embodiments, in the post-fixation step, the sample is treated with the aldehyde-containing fixative for about 18 hours. In some embodiments, in the post-fixation step, the sample is treated with the aldehyde-containing fixative for about 19 hours. In some embodiments, in the post-fixation step, the sample is treated with the aldehyde-containing fixative for about 20 hours.

In some embodiments, in the post-fixation step, the sample is treated with formaldehyde for about 2 to about 30 hours. In some embodiments, in the post-fixation step, the sample is treated with formaldehyde for about 2 to about 25 hours. In some embodiments, in the post-fixation step, the sample is treated with formaldehyde for about 2 to about 20 hours. In some embodiments, in the post-fixation step, the sample is treated with formaldehyde for about 2 to about 18 hours. In some embodiments, in the post-fixation step, the sample is treated with formaldehyde for about 2 to about 15 hours. In some embodiments, in the post-fixation step, the sample is treated with formaldehyde for about 2 to about 10 hours. In some embodiments, in the post-fixation step, the sample is treated with formaldehyde for about 2 to about 5 hours. In some embodiments, in the post-fixation step, the sample is treated with formaldehyde for about 2 hours. In some embodiments, in the post-fixation step, the sample is treated with formaldehyde for about 3 hours. In some embodiments, in the post-fixation step, the sample is treated with formaldehyde for about 4 hours. In some embodiments, in the post-fixation step, the sample is treated with formaldehyde for about 5 hours. In some embodiments, in the post-fixation step, the sample is treated with formaldehyde for about 6 hours. In some embodiments, in the post-fixation step, the sample is treated with formaldehyde for about 7 hours. In some embodiments, in the post-fixation step, the sample is treated with formaldehyde for about 8 hours. In some embodiments, in the post-fixation step, the sample is treated with formaldehyde for about 9 hours. In some embodiments, in the post-fixation step, the sample is treated with formaldehyde for about 10 hours. In some embodiments, in the post-fixation step, the sample is treated with formaldehyde for about 11 hours. In some embodiments, in the post-fixation step, the sample is treated with formaldehyde for about 12 hours. In some embodiments, in the post-fixation step, the sample is treated with formaldehyde for about 13 hours. In some embodiments, in the post-fixation step, the sample is treated with formaldehyde for about 14 hours. In some embodiments, in the post-fixation step, the sample is treated with formaldehyde for about 15 hours. In some embodiments, in the post-fixation step, the sample is treated with formaldehyde for about 16 hours. In some embodiments, in the post-fixation step, the sample is treated with formaldehyde for about 17 hours. In some embodiments, in the post-fixation step, the sample is treated with formaldehyde for about 18 hours. In some embodiments, in the post-fixation step, the sample is treated with formaldehyde for about 19 hours. In some embodiments, in the post-fixation step, the sample is treated with formaldehyde for about 20 hours.

In some specific embodiments, in the post-fixation step, the sample is treated with an aldehyde-containing fixative comprising less than about 12% formaldehyde for more than 15 hours. In some specific embodiments, in the post-fixation step, the sample is treated with an aldehyde-containing fixative comprising less than about 12% formaldehyde for about 18 hours. In some specific embodiments, in the post-fixation step, the sample is treated with an aldehyde-containing fixative comprising less than about 12% formaldehyde for about 19 hours. In some specific embodiments, in the post-fixation step, the sample is treated with an aldehyde-containing fixative comprising less than about 12% formaldehyde for about 20 hours. In some specific embodiments, in the post-fixation step, the sample is treated with an aldehyde-containing fixative comprising less than about 12% formaldehyde for about 25 hours.

In other specific embodiments, in the post-fixation step, the sample is treated with an aldehyde-containing fixative comprising about 12% or more formaldehyde for less than 10 hours. In other specific embodiments, in the post-fixation step, the sample is treated with an aldehyde-containing fixative comprising about 12% or more formaldehyde for about 10 hours. In other specific embodiments, in the post-fixation step, the sample is treated with an aldehyde-containing fixative comprising about 12% or more formaldehyde for about 9 hours. In other specific embodiments, in the post-fixation step, the sample is treated with an aldehyde-containing fixative comprising about 12% or more formaldehyde for about 8 hours. In other specific embodiments, in the post-fixation step, the sample is treated with an aldehyde-containing fixative comprising about 12% or more formaldehyde for about 7 hours. In other specific embodiments, in the post-fixation step, the sample is treated with an aldehyde-containing fixative comprising about 12% or more formaldehyde for about 6 hours. In other specific embodiments, in the post-fixation step, the sample is treated with an aldehyde-containing fixative comprising about 12% or more formaldehyde for about 5 hours. In other specific embodiments, in the post-fixation step, the sample is treated with an aldehyde-containing fixative comprising about 12% or more formaldehyde for about 4 hours. In other specific embodiments, in the post-fixation step, the sample is treated with an aldehyde-containing fixative comprising about 12% or more formaldehyde for about 3 hours. In other specific embodiments, in the post-fixation step, the sample is treated with an aldehyde-containing fixative comprising about 12% or more formaldehyde for about 2 hours.

In some specific embodiments, the aldehyde-containing fixative is in a buffer with a pH of about 6. In some specific embodiments, the aldehyde-containing fixative is in a buffer with a pH of about 6.5. In some specific embodiments, the aldehyde-containing fixative is in a buffer with a pH of about 7. In some specific embodiments, the aldehyde-containing fixative is in a buffer with a pH of about 7.5. In some specific embodiments, the aldehyde-containing fixative is in a buffer with a pH of about 8. In some specific embodiments, the aldehyde-containing fixative is in a buffer with a pH of about 8.5. In some specific embodiments, the aldehyde-containing fixative is in a buffer with a pH of about 9.

In some embodiments, the post-fixation step is carried out at a temperature of about 4-50° C. In some embodiments, the post-fixation step is carried out at a temperature of about 4° C. In some embodiments, the post-fixation step is carried out at a temperature of about 10° C. In some embodiments, the post-fixation step is carried out at a temperature of about 20° C. In some embodiments, the post-fixation step is carried out at a temperature of about 25° C. In some embodiments, the post-fixation step is carried out at a temperature of about 30° C. In some embodiments, the post-fixation step is carried out at a temperature of about 40° C. In some embodiments, the post-fixation step is carried out at a temperature of about 50° C. In some embodiments, the post-fixation step is carried out at ambient temperature.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being equal or higher than about 12%, and wherein the post-fixation step is carried out at a temperature of about 4° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being equal or higher than about 12%, and wherein the post-fixation step is carried out at a temperature of about 4° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being equal or higher than about 12%, and wherein the post-fixation step is carried out at a temperature of about 4° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being equal or higher than about 12%, and wherein the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being equal or higher than about 12%, and wherein the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being equal or higher than about 12%, and wherein the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being equal or higher than about 12%, and wherein the post-fixation step is carried out at a temperature of about 50° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being equal or higher than about 12%, and wherein the post-fixation step is carried out at a temperature of about 50° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hour. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being equal or higher than about 12%, and wherein the post-fixation step is carried out at a temperature of about 50° C. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours. In one embodiment, the post-fixation step lasts for about 4 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being less than about 12%, and wherein the post-fixation step is carried out at a temperature of about 4° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being less than about 12%, and wherein the post-fixation step is carried out at a temperature of about 4° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being less than about 12%, and wherein the post-fixation step is carried out at a temperature of about 4° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being less than about 12%, and wherein the post-fixation step is carried out at ambient temperature. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being less than about 12%, and wherein the post-fixation step is carried out at ambient temperature. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being less than about 12%, and wherein the post-fixation step is carried out at ambient temperature. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 6 and its aldehyde percentage being less than about 12%, and wherein the post-fixation step is carried out at a temperature of about 50° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 7 and its aldehyde percentage being less than about 12%, and wherein the post-fixation step is carried out at a temperature of about 50° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with an aldehyde-containing fixative, wherein the aldehyde-containing fixative is in an isotonic buffer with a pH at about 8 and its aldehyde percentage being less than about 12%, and wherein the post-fixation step is carried out at a temperature of about 50° C. In one embodiment, the post-fixation step lasts for about 2 hours. In one embodiment, the post-fixation step lasts for about 3 hours. In one embodiment, the post-fixation step lasts for about 4 hours. In one embodiment, the post-fixation step lasts for about 5 hours. In one embodiment, the post-fixation step lasts for about 6 hours. In one embodiment, the post-fixation step lasts for about 7 hours. In one embodiment, the post-fixation step lasts for about 8 hours. In one embodiment, the post-fixation step lasts for about 9 hours. In one embodiment, the post-fixation step lasts for about 10 hours. In one embodiment, the post-fixation step lasts for about 11 hours. In one embodiment, the post-fixation step lasts for about 12 hours. In one embodiment, the post-fixation step lasts for about 13 hours. In one embodiment, the post-fixation step lasts for about 14 hours. In one embodiment, the post-fixation step lasts for about 15 hours. In one embodiment, the post-fixation step lasts for about 16 hours. In one embodiment, the post-fixation step lasts for about 16 hours. In one embodiment, the post-fixation step lasts for about 17 hours. In one embodiment, the post-fixation step lasts for about 18 hours. In one embodiment, the post-fixation step lasts for about 24 hours. In one embodiment, the post-fixation step lasts for about 36 hours. In one embodiment, the post-fixation step lasts for about 48 hours.

In certain embodiments, the method for preparing a biological sample for in situ hybridization provided herein comprises a post-fixation step with formaldehyde equal or higher than about 12% in an isotonic buffer with a neutral or near neutral pH, and the post-fixation step is carried out at ambient temperature. In one embodiment, the post-fixation step lasts for about 0.5 hour. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours.

In certain embodiments, the method for preparing a biological sample for in situ hybridization provided herein comprises a post-fixation step with formaldehyde below about 12% in an isotonic buffer with a neutral or near neutral pH, and the post-fixation step is carried out at ambient temperature. In one embodiment, the post-fixation step lasts for about 12 hours. In one embodiment, the post-fixation step lasts for about 14 hours. In one embodiment, the post-fixation step lasts for about 16 hours. In one embodiment, the post-fixation step lasts for about 18 hours. In one embodiment, the post-fixation step lasts for about 20 hours. In one embodiment, the post-fixation step lasts for about 22 hours. In one embodiment, the post-fixation step lasts for about 24 hours.

In certain embodiments, the method for preparing a biological sample for in situ hybridization provided herein comprises a post-fixation step with about 12% formaldehyde in phosphate buffered saline, and the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours.

In certain embodiments, the method for preparing a biological sample for in situ hybridization provided herein comprises a post-fixation step with about 24% formaldehyde in phosphate buffered saline, and the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours.

In certain embodiments, the method for preparing a biological sample for in situ hybridization provided herein comprises a post-fixation step with about 37% formaldehyde in phosphate buffered saline, and the post-fixation step is carried out at ambient temperature. In one embodiment, the post-fixation step lasts for about 1 hour. In one embodiment, the post-fixation step lasts for about 1.5 hours. In one embodiment, the post-fixation step lasts for about 2 hours. In one embodiment, the post-fixation step lasts for about 2.5 hours. In one embodiment, the post-fixation step lasts for about 3 hours. In one embodiment, the post-fixation step lasts for about 3.5 hours.

In certain embodiments, the method for preparing a biological sample for in situ hybridization provided herein comprises a post-fixation step with 10% neutral buffered formalin, and the post-fixation step is carried out at ambient temperature. In one embodiment, the post-fixation step lasts for about 12 hours. In one embodiment, the post-fixation step lasts for about 14 hours. In one embodiment, the post-fixation step lasts for about 16 hours. In one embodiment, the post-fixation step lasts for about 18 hours. In one embodiment, the post-fixation step lasts for about 20 hours. In one embodiment, the post-fixation step lasts for about 22 hours. In one embodiment, the post-fixation step lasts for about 24 hours.

In some embodiments of the various methods provided herein, the sample was prepared for in situ hybridization. In some embodiments, the in situ hybridization is for detecting a target nucleic acid comprising less than 100 nucleotides. In some embodiments, the target nucleic acid comprises 15-100 nucleotides. In some embodiments, the target nucleic acid comprises 15-80 nucleotides. In some embodiments, the target nucleic acid comprises 15-60 nucleotides. In some embodiments, the target nucleic acid comprises 15-50 nucleotides. In some embodiments, the target nucleic acid comprises 15-40 nucleotides. In some embodiments, the target nucleic acid comprises less than 90 nucleotides. In some embodiments, the target nucleic acid comprises less than 80 nucleotides. In some embodiments, the target nucleic acid comprises less than 70 nucleotides. In some embodiments, the target nucleic acid comprises less than 60 nucleotides. In some embodiments, the target nucleic acid comprises less than 50 nucleotides. In some embodiments, the target nucleic acid comprises less than 40 nucleotides. In some embodiments, the target nucleic acid comprises less than 30 nucleotides. In some embodiments, the target nucleic acid comprises less than 20 nucleotides. In some embodiments, the target nucleic acid comprises less than 16 nucleotides. In some embodiments, the in situ hybridization is for detecting DNA. In some embodiments, the in situ hybridization is for detecting RNA. The method provided herein can also be used to detect longer nucleic acid, e.g., comprising more than 100, 200, 300, 500, 1000 or more nucleotides.

In some embodiments, the method of preparing a biological sample provided herein is for RNA in situ hybridization. In some embodiments, the method for preparing a biological sample for in situ hybridization is for detecting small RNA species. In one embodiment, the RNA detected is less than 100 nucleotides. In one embodiment, the RNA detected is less than 50 nucleotides. In one embodiment, the RNA detected is less than 40 nucleotides. In one embodiment, the RNA detected is between 10 and 40 nucleotides. In one embodiment, the RNA detected is between 15 and 40 nucleotides. In one embodiment, the RNA detected is between 30 and 40 nucleotides.

In one embodiment, the method is for detecting sncRNAs. In one embodiment, the method is for detecting miRNAs. In one embodiment, the method is for detecting siRNAs. In one embodiment, the method is for detecting piRNAs. In one embodiment, the method is for detecting endogenous RNAs. In another embodiment, the method is for detecting exogenous RNAs. sncRNAs have emerged as valuable therapeutics for disease intervention with the ability to efficiently modulate gene expression in clinically relevant model systems (Watts et al., Journal of Pathology, 226(2), 365-379, 2012; Schoch et al., Neuron Review, 94, 1056-1070, 2017). miRNAs are naturally occurring small (~22 nucleotide) regulatory RNAs present in all multicellular organisms, single-cell alga, and some viruses (Molnar et al., Nature, 447(7148), 2007; Bartel, Cell, 173, 20-51, 2018). To date more than 15,000 miRNAs from animals, plants and viruses have been registered (www.mirbase.org), many expressed in a tissue, cell-type, and cell-state specific manner. Deregulation of miRNA expression may lead to severe conditions, such as neurological disorders, infertility, immune disorders or cancers.

In some embodiments, the method provided herein is for detecting naturally occurring small nucleic acids. Naturally occurring small nucleic acids play crucial and diverse cellular functions from transcription and RNA processing to translation. A common feature of these RNAs is their size ranging from 15 and 40 nucleotides long. In other embodiments, the method provided herein is for detecting synthetic small nucleic acids.

In some embodiments, the method for preparing a biological sample for in situ hybridization provided herein comprises the biological sample of various sources. In one embodiment, the biological sample is a tissue specimen or is derived from a tissue specimen. In one embodiment, the biological sample is a blood sample or is derived from a blood sample. In one embodiment, the biological sample is a cytological sample or is derived from a cytological sample.

In one embodiment, the biological sample is cultured cells. In another embodiment, the biological sample is an exosome.

Tissue specimens include, for example, tissue biopsy samples. Blood samples include, for example, blood samples taken for diagnostic purposes. In the case of a blood sample, the blood can be directly analyzed, such as in a blood smear, or the blood can be processed, for example, lysis of red blood cells, isolation of PBMCs or leukocytes, isolation of target cells, and the like, such that the cells in the sample analyzed by methods of the disclosure are in a blood sample or are derived from a blood sample. Similarly, a tissue specimen can be processed, for example, the tissue specimen minced and treated physically or enzymatically to disrupt the tissue into individual cells or cell clusters. Additionally, a cytological sample can be processed to isolate cells or disrupt cell clusters, if desired. Thus, the tissue, blood and cytological samples can be obtained and processed using methods well known in the art. The methods of the disclosure can be used in diagnostic applications to identify the presence or absence of pathological cells based on the presence or absence of a nucleic acid target that is a biomarker indicative of a pathology.

It is understood by those skilled in the art that any of a number of suitable samples can be used for detecting target nucleic acids using methods provided herein. The sample for use in the methods provided herein is generally a biological sample or tissue sample. Such a sample can be obtained from a biological subject, including a sample of biological tissue or fluid origin that is collected from an individual or some other source of biological material such as biopsy, autopsy or forensic materials. A biological sample also includes samples from a region of a biological subject containing or suspected of containing precancerous or cancer cells or tissues, for example, a tissue biopsy, including fine needle aspirates, blood sample or cytological specimen. Such samples can be, but are not limited to, organs, tissues, tissue fractions, cells, and/or exosomes isolated from an organism such as a mammal. Exemplary biological samples include, but are not limited to, a cell culture, including a primary cell culture, a cell line, a tissue, an organ, an organelle, a biological fluid, and the like. Additional biological samples include but are not limited to a skin sample, tissue biopsies, including fine needle aspirates, cytological samples, stool, bodily fluids, including blood and/or serum samples, saliva, semen, and the like. Such samples can be used for medical or veterinary diagnostic purposes.

Collection of cytological samples for analysis by methods provided herein are well known in the art (see, for example, Dey, "Cytology Sample Procurement, Fixation and Processing" in *Basic and Advanced Laboratory Techniques in Histopathology and Cytology* pp. 121-132, Springer, Singapore (2018); "Non-Gynecological Cytology Practice Guideline" American Society of Cytopathology, Adopted by the ASC executive board Mar. 2, 2004).

For example, methods for processing samples for analysis of cervical tissue, including tissue biopsy and cytology samples, are well known in the art (see, for example, *Cecil Textbook of Medicine*, Bennett and Plum, eds., 20th ed., WB Saunders, Philadelphia (1996); *Colposcopy and Treatment of Cervical Intraepithelial Neoplasia: A Beginner's Manual*, Sellors and Sankaranarayanan, eds., International Agency for Research on Cancer, Lyon, France (2003); Kalaf and Cooper, *J. Clin. Pathol.* 60:449-455 (2007); Brown and Trimble, *Best Pract Res. Clin. Obstet. Gynaecol.* 26:233-242 (2012); Waxman et al., *Obstet. Gynecol.* 120:1465-1471 (2012); *Cervical Cytology Practice Guidelines TOC*, Approved by the American Society of Cytopathology (ASC) Executive Board, Nov. 10, 2000)).

In particular embodiments, the sample is a tissue specimen or is derived from a tissue specimen. In some embodiments, the tissue specimen is formalin-fixed paraffin-embedded (FFPE). In some embodiments, the tissue specimen is fresh frozen. In some embodiments, the tissue specimen is prepared with a fixative other than formalin. In some embodiments, the fixative other than formalin is selected from the group consisting of ethanol, methanol, Bouin's fixative, B5, and I.B.F. In other particular embodiments, the sample is a blood sample or is derived from a blood sample. In still other particular embodiments, the sample is a cytological sample or is derived from a cytological sample.

5.3 Methods of Detecting a Target Nucleic Acid

In another aspect, provided herein is a method for detecting a target nucleic acid in a cell, comprising preparing a biological sample according to the methods provided herein, for example, as described in Section 5.2 above, and conducting in situ hybridization detection assay with a set of one or more probes hybridizing to the target nucleic acid.

In some embodiments, the method of in situ detection of a target nucleic acid in a previously fixed sample provided herein comprises applying an aldehyde-containing fixative to the sample, and conducting in situ hybridization detection assay with a set of one or more probes hybridizing to the target nucleic acid.

In some embodiments, the in situ hybridization is for detecting DNA. In some embodiments, the in situ hybridization is for detecting RNA.

In some embodiments, the method provided herein detects relatively short nucleic acid. For example, in some embodiments, the in situ hybridization is for detecting a target nucleic acid comprising less than 100 nucleotides. In some embodiments, the target nucleic acid comprises 15-100 nucleotides. In some embodiments, the target nucleic acid comprises 15-80 nucleotides. In some embodiments, the target nucleic acid comprises 15-60 nucleotides. In some embodiments, the target nucleic acid comprises 15-50 nucleotides. In some embodiments, the target nucleic acid comprises 15-40 nucleotides. In some embodiments, the target nucleic acid comprises less than 90 nucleotides. In some embodiments, the target nucleic acid comprises less than 80 nucleotides. In some embodiments, the target nucleic acid comprises less than 70 nucleotides. In some embodiments, the target nucleic acid comprises less than 60 nucleotides. In some embodiments, the target nucleic acid comprises less than 50 nucleotides. In some embodiments, the target nucleic acid comprises less than 40 nucleotides. In some embodiments, the target nucleic acid comprises less than 30 nucleotides. In some embodiments, the target nucleic acid comprises less than 20 nucleotides. In some embodiments, the target nucleic acid comprises less than 16 nucleotides. In some embodiments, the in situ hybridization is for detecting small RNA species. In one embodiment, the RNA detected is less than 100 nucleotides. In one embodiment, the RNA detected is less than 50 nucleotides. In one embodiment, the RNA detected is less than 40 nucleotides. In one embodiment, the RNA detected is between 10 and 40 nucleotides. In one embodiment, the RNA detected is between 15 and 40 nucleotides. In one embodiment, the RNA detected is between 30 and 40 nucleotides. In one embodiment, the method is for detecting sncRNAs. In one embodiment, the method is for detecting miRNAs. In one embodiment, the method is for detecting siRNAs. In one embodiment, the method is for detecting piRNAs. In one embodiment, the method is for detecting ASOs. In one embodiment, the method is for detecting endogenous RNAs. In one embodiment, the method is for detecting exogenous RNAs.

The method provided herein can also be used to detect relatively long nucleic acid, e.g., comprising more than 100, 200, 300, 500, 1000, or more nucleotides.

Methods for in situ detection of nucleic acids are well known to those skilled in the art (see, for example, US 2008/0038725; US 2009/0081688; Hicks et al., J. Mol. Histol. 35:595-601 (2004)). As used herein, "in situ hybridization" or "ISH" refers to a type of hybridization that uses a directly or indirectly labeled complementary DNA or RNA strand, such as a probe, to bind to and localize a specific nucleic acid, in a sample, in particular a portion or section of tissue or cells (in situ). The probe types can be double stranded DNA (dsDNA), single stranded DNA (ssDNA), single stranded complimentary RNA (sscRNA), messenger RNA (mRNA), micro RNA (miRNA), ribosomal RNA, mitochondrial RNA, and/or synthetic oligonucleotides.

In some embodiments, the in situ hybridization provided herein comprises providing at least one set of one or more target probe(s) capable of hybridizing to said target nucleic acid; providing a signal-generating complex capable of hybridizing to said set of one or more target probe(s), said signal-generating complex comprises a nucleic acid component capable of hybridizing to said set of one or more target probe(s) and a label probe; hybridizing said target nucleic acid to said set of one or more target probe(s); and capturing the signal-generating complex to said set of one or more target probe(s) and thereby capturing the signal-generating complex to said target nucleic acid.

In some embodiments, each set of one or more target probe(s) comprises a single probe. In other embodiments, each set of one or more target probe(s) comprises two probes. In yet other embodiments, each set of one or more target probe(s) comprises more than two probes.

In some embodiments, when each set of target probes comprises a single target probe, a signal-generating complex is formed when the single target probe is bound to the target nucleic acid. In other embodiments, when each set of target probes comprise two target probes, a signal-generating complex is formed when both members of a target probe pair are bound to the target nucleic acid.

In some specific embodiments, the RNA ISH used herein is RNAscope®, which is described in more detail in, e.g., U.S. Pat. Nos. 7,709,198, 8,604,182, and 8,951,726. Specifically, RNAscope® describes using specially designed oligonucleotide probes in combination with a branched-DNA-like signal-generating complex to reliably detect RNA as small as 1 kilobase at single-molecule sensitivity under standard bright-field microscopy (Anderson et al., J. Cell. Biochem. 117(10):2201-2208 (2016); Wang et al., J. Mol. Diagn. 14(1):22-29 (2012)).

In some embodiments, each target probe comprises a target (T) section and a label (L) section, wherein the T section is a nucleic acid sequence complementary to a section on the target nucleic acid and the L section is a nucleic acid sequence complementary to a section on the nucleic acid component of the signal-generating complex, and wherein the T sections of the one or more target probe(s) are complementary to non-overlapping regions of the target nucleic acid, and the L sections of the one or more target probe(s) are complementary to non-overlapping regions of the nucleic acid component of the generating complex.

In some embodiments, one set of one or more target probe(s) is used to detect a target nucleic acid. In other embodiments, two or more sets of one or more target probe(s) are used to detect a target nucleic acid. In some embodiments, two sets of one or more target probe(s) are used to detect a target nucleic acid. In some embodiments, three sets of one or more target probe(s) are used to detect a target nucleic acid. In some embodiments, four sets of one or more target probe(s) are used to detect a target nucleic acid. In some embodiments, five sets of one or more target probe(s) are used to detect a target nucleic acid. In some embodiments, six sets of one or more target probe(s) are used to detect a target nucleic acid. In some embodiments, seven sets of one or more target probe(s) are used to detect a target nucleic acid. In some embodiments, eight sets of one or more target probe(s) are used to detect a target nucleic acid. In some embodiments, nine sets of one or more target probe(s) are used to detect a target nucleic acid. In some embodiments, ten sets of one or more target probe(s) are used to detect a target nucleic acid. In some embodiments, more than 10 sets of one or more target probe(s) are used to detect a target nucleic acid. In some embodiments, more than 15 sets of one or more target probe(s) are used to detect a target nucleic acid. In some embodiments, more than 20 sets of one or more target probe(s) are used to detect a target nucleic acid. In some embodiments, more than 30 sets of one or more target probe(s) are used to detect a target nucleic acid.

In some embodiments, the method provided herein is for detecting multiple nucleic acid targets. In some embodiments, the multiple nucleic acid targets all comprise less than 100 nucleotides. In other embodiments, some of the nucleic acid targets comprise less than 100 nucleotides, while other targets comprise more than 100 nucleotides.

As used herein, a "target probe" is a polynucleotide that is capable of hybridizing to a target nucleic acid and capturing or binding a label probe or signal-generating complex (SGC) component to that target nucleic acid. The target probe can hybridize directly to the label probe, or it can hybridize to one or more nucleic acids that in turn hybridize to the label probe; for example, the target probe can hybridize to an amplifier, a pre-amplifier or a pre-pre-amplifier in an SGC. The target probe thus includes a first polynucleotide sequence that is complementary to a polynucleotide sequence of the target nucleic acid and a second polynucleotide sequence that is complementary to a polynucleotide sequence of the label probe, amplifier, pre-amplifier, pre-pre-amplifier, or the like. The target probe is generally single stranded so that the complementary sequence is available to hybridize with a corresponding target nucleic acid, label probe, amplifier, pre-amplifier or pre-pre-amplifier. In some embodiments, the target probes are provided as a pair.

As used herein, the term "label probe" refers to an entity that binds to a target molecule, directly or indirectly, generally indirectly, and allows the target to be detected. A label probe (or "LP") contains a nucleic acid binding portion that is typically a single stranded polynucleotide or oligonucleotide that comprises one or more labels which directly or indirectly provides a detectable signal. The label can be covalently attached to the polynucleotide, or the polynucleotide can be configured to bind to the label. For example, a biotinylated polynucleotide can bind a streptavidin-associated label. The label probe can, for example, hybridize directly to a target nucleic acid. In general, the label probe can hybridize to a nucleic acid that is in turn hybridized to the target nucleic acid or to one or more other nucleic acids that are hybridized to the target nucleic acid. Thus, the label probe can comprise a polynucleotide sequence that is complementary to a polynucleotide sequence, particularly a portion, of the target nucleic acid. Alternatively, the label probe can comprise at least one polynucleotide sequence that is complementary to a polynucleotide sequence in an amplifier, pre-amplifier, or pre-pre-amplifier in a SGC.

In some embodiments, the SGC provided herein comprises additional comments such an amplifier, a pre-amplifier, and/or a pre-pre-amplifier.

As used herein, an "amplifier" is a molecule, typically a polynucleotide, that is capable of hybridizing to multiple label probes. Typically, the amplifier hybridizes to multiple identical label probes. The amplifier can also hybridize to a target nucleic acid, to at least one target probe of a pair of target probes, to both target probes of a pair of target probes, or to nucleic acid bound to a target probe such as an amplifier, pre-amplifier or pre-pre-amplifier. For example, the amplifier can hybridize to at least one target probe and to a plurality of label probes, or to a pre-amplifier and a plurality of label probes. The amplifier can be, for example, a linear, forked, comb-like, or branched nucleic acid. As described herein for all polynucleotides, the amplifier can include modified nucleotides and/or nonstandard internucleotide linkages as well as standard deoxyribonucleotides, ribonucleotides, and/or phosphodiester bonds. Suitable amplifiers are described, for example, in U.S. Pat. Nos. 5,635,352, 5,124,246, 5,710,264, 5,849,481, and 7,709,198 and U.S. publications 2008/0038725 and 2009/0081688, each of which is incorporated by reference.

As used herein, a "pre-amplifier" is a molecule, typically a polynucleotide, that serves as an intermediate binding component between one or more target probes and one or more amplifiers. Typically, the pre-amplifier hybridizes simultaneously to one or more target probes and to a plurality of amplifiers. Exemplary pre-amplifiers are described, for example, in U.S. Pat. Nos. 5,635,352, 5,681, 697 and 7,709,198 and U.S. publications 2008/0038725, 2009/0081688 and 2017/0101672, each of which is incorporated by reference.

As used herein, a "pre-pre-amplifier" is a molecule, typically a polynucleotide, that serves as an intermediate binding component between one or more target probes and one or more pre-amplifiers. Typically, the pre-pre-amplifier hybridizes simultaneously to one or more target probes and to a plurality of pre-amplifiers. Exemplary pre-pre-amplifiers are described, for example, in 2017/0101672, which is incorporated by reference.

A label is typically used in RNA in situ hybridization for detecting target nucleic acid. As used herein, a "label" is a moiety that facilitates detection of a molecule. Common labels include fluorescent, luminescent, light-scattering, and/or colorimetric labels. Suitable labels include enzymes, and fluorescent and chromogenic moieties, as well as radionuclides, substrates, cofactors, inhibitors, chemiluminescent moieties, magnetic particles, rare earth metals, metal isotopes, and the like. In a particular embodiment, the label is an enzyme. Exemplary enzyme labels include, but are not limited to horseradish peroxidase (HRP), alkaline phosphatase (AP), β-galactosidase, glucose oxidase, and the like, as well as various proteases. Other labels include, but are not limited to, fluorophores, dinitrophenyl (DNP), and the like. Labels are well known to those skilled in the art, as described, for example, in Hermanson, *Bioconjugate Techniques*, Academic Press, San Diego (1996), and U.S. Pat. Nos. 3,817,837; 3,850,752; 3,939,350; 3,996,345; 4,277, 437; 4,275,149; and 4,366,241. Many labels are commercially available and can be used in methods and assays of the disclosure, including detectable enzyme/substrate combinations (Pierce, Rockford IL; Santa Cruz Biotechnology, Dallas TX; Life Technologies, Carlsbad CA). In a particular embodiment of the disclosure, the enzyme can utilize a chromogenic or fluorogenic substrate to produce a detectable signal, as described herein. Exemplary labels are described herein.

Any of a number of enzymes or non-enzyme labels can be utilized so long as the enzymatic activity or non-enzyme label, respectively, can be detected. The enzyme thereby produces a detectable signal, which can be utilized to detect a target nucleic acid. Particularly useful detectable signals are chromogenic or fluorogenic signals. Accordingly, particularly useful enzymes for use as a label include those for which a chromogenic or fluorogenic substrate is available. Such chromogenic or fluorogenic substrates can be converted by enzymatic reaction to a readily detectable chromogenic or fluorescent product, which can be readily detected and/or quantified using microscopy or spectroscopy. Such enzymes are well known to those skilled in the art, including but not limited to, horseradish peroxidase, alkaline phosphatase, β-galactosidase, glucose oxidase, and the like (see Hermanson, *Bioconjugate Techniques*, Academic Press, San Diego (1996)). Other enzymes that have well known chromogenic or fluorogenic substrates include various peptidases, where chromogenic or fluorogenic peptide substrates can be utilized to detect proteolytic cleavage reactions. The use of chromogenic and fluorogenic substrates is also well known in bacterial diagnostics, including but not limited to the use of α- and β-galactosidase, β-glucuronidase, 6-phospho-β-D-galactoside 6-phosphogalactohydrolase, β-glucosidase, α-glucosidase, amylase, neuraminidase, esterases, lipases, and the like (Manafi et al., *Microbiol. Rev.* 55:335-348 (1991)), and such enzymes with known chromogenic or fluorogenic substrates can readily be adapted for use in methods provided herein.

Various chromogenic or fluorogenic substrates to produce detectable signals are well known to those skilled in the art and are commercially available. Exemplary substrates that can be utilized to produce a detectable signal include, but are not limited to, 3,3'-diaminobenzidine (DAB), 3,3',5,5'-tetramethylbenzidine (TMB), chloronaphthol (4-CN) (4-chloro-1-naphthol), 2,2'-azino-bis(3-ethylbenzothiazoline-6-sulphonic acid) (ABTS), o-phenylenediamine dihydrochloride (OPD), and 3-amino-9-ethylcarbazole (AEC) for horseradish peroxidase; 5-bromo-4-chloro-3-indolyl-1-phosphate (BCIP), nitroblue tetrazolium (NBT), Fast Red (Fast Red TR/AS-MX), and p-nitrophenyl phosphate (PNPP) for alkaline phosphatase; 1-methyl-3-indolyl-β-D-galactopyranoside and 2-methoxy-4-(2-nitrovinyl)phenyl β-D-galactopyranoside for β-galactosidase; 2-methoxy-4-(2-nitrovinyl)phenyl β-D-glucopyranoside for β-glucosidase; and the like. Exemplary fluorogenic substrates include, but are not limited to, 4-(trifluoromethyl)umbelliferyl phosphate for alkaline phosphatase; 4-methylumbelliferyl phosphate bis (2-amino-2-methyl-1,3-propanediol), 4-methylumbelliferyl phosphate bis (cyclohexylammonium) and 4-methylumbelliferyl phosphate for phosphatases; QuantaBlu™ and Quintolet for horseradish peroxidase; 4-methylumbelliferyl β-D-galactopyranoside, fluorescein di(β-D-galactopyranoside) and naphthofluorescein di-(β-D-galactopyranoside) for β-galactosidase; 3-acetylumbelliferyl β-D-glucopyranoside and 4-methylumbelliferyl-β-D-glucopyranoside for β-glucosidase; and 4-methylumbelliferyl-α-D-galactopyranoside for α-galactosidase. Exemplary enzymes and substrates for producing a detectable signal are also described, for example, in US publication 2012/0100540. Various detectable enzyme substrates, including chromogenic or fluorogenic substrates, are well known and commercially available (Pierce, Rockford IL; Santa Cruz Biotechnology, Dallas TX; Invitrogen, Carlsbad CA; 42 Life Science; Biocare). Generally, the substrates are converted to products that form precipitates that are deposited at the site of the target nucleic acid. Other exemplary substrates include, but are not limited to, HRP-Green (42 Life Science), Betazoid DAB, Cardassian DAB, Romulin AEC, Bajoran Purple, Vina Green, Deep Space Black™, Warp Red™, Vulcan Fast Red and Ferangi Blue from Biocare (Concord CA; biocare.net/products/detection/chromogens).

Exemplary rare earth metals and metal isotopes suitable as a detectable label include, but are not limited to, lanthanide (III) isotopes such as 141Pr, 142Nd, 143Nd, 144Nd, 145Nd, 146Nd, 147Sm, 148Nd, 149Sm, 150Nd, 151Eu, 152Sm, 153Eu, 154Sm, 155Gd, 156Gd, 158Gd, 159Tb, 160Gd, 161Dy, 162Dy, 163Dy, 164Dy, 165Ho, 166Er, 167Er, 168Er, 169Tm, 170Er, 171Yb, 172Yb, 173Yb, 174Yb, 175Lu, and 176Yb. Metal isotopes can be detected, for example, using time-of-flight mass spectrometry (TOF-MS) (for example, Fluidigm Helios and Hyperion systems, fluidigm.com/systems; South San Francisco, CA).

Biotin-avidin (or biotin-streptavidin) is a well-known signal amplification system based on the fact that the two molecules have extraordinarily high affinity to each other and that one avidin/streptavidin molecule can bind four biotin molecules. Antibodies are widely used for signal amplification in immunohistochemistry and ISH. Tyramide signal amplification (TSA) is based on the deposition of a large number of haptenized tyramide molecules by peroxidase activity. Tyramine is a phenolic compound. In the presence of small amounts of hydrogen peroxide, immobilized horseradish peroxidase (HRP) converts the labeled substrate into a short-lived, extremely reactive intermediate. The activated substrate molecules then very rapidly react with and covalently bind to electron-rich moieties of proteins, such as tyrosine, at or near the site of the peroxidase binding site. In this way, many hapten molecules conjugated to tyramide can be introduced at the hybridization site in situ. Subsequently, the deposited tyramide-hapten molecules can be visualized directly or indirectly. Such a detection system is described in more detail, for example, in U.S. publication 2012/0100540.

Embodiments described herein can utilize enzymes to generate a detectable signal using appropriate chromogenic or fluorogenic substrates. It is understood that, alternatively, a label probe can have a detectable label directly coupled to the nucleic acid portion of the label probe. Exemplary detectable labels are well known to those skilled in the art, including but not limited to chromogenic or fluorescent labels (see Hermanson, *Bioconjugate Techniques*, Academic Press, San Diego (1996)). Exemplary fluorophores useful as labels include, but are not limited to, rhodamine derivatives, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like; 7-nitrobenz-2-oxa-1,3-diazole (NBD); fluorescein and derivatives thereof; napthalenes such as dansyl (5-dimethylaminonapthalene-1-sulfonyl); coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like; 4,4-difluoro-4-bora-3a,4a-diaza-s-indacene (BODIPY™) and derivatives thereof (Molecular Probes; Eugene, OR); pyrenes and sulfonated pyrenes such as Cascade Blue™ and derivatives thereof, including 8-methoxypyrene-1,3,6-trisulfonic acid, and the like; pyridyloxazole derivatives and dapoxyl derivatives (Molecular Probes); Lucifer Yellow (3,6-disulfonate-4-amino-naphthalimide) and derivatives thereof; CyDye™ fluorescent dyes (Amersham/GE Healthcare Life Sciences; Piscataway NJ), ATTO 390, DyLight 395XL, ATTO 425, ATTO 465, ATTO 488, ATTO 490LS, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 643, ATTO 647, ATTO 647N, ATTO 655, ATTO Oxa12, ATTO 665, ATTO 680, ATTO 700, ATTO 725, ATTO 740, Cyan 500 NHS-Ester (ATTO-TECH, Siegen, Germany), and the like. Exemplary chromophores include, but are not limited to, phenolphthalein, malachite green, nitroaromatics such as nitrophenyl, diazo dyes, dabsyl (4-dimethylaminoazobenzene-4'-sulfonyl), and the like.

As disclosed herein, the methods provided herein can be used for concurrent detection of multiple target nucleic acids. In the case of using fluorophores as labels, the fluorophores to be used for detection of multiple target nucleic acids are selected so that each of the fluorophores are distinguishable and can be detected concurrently in the fluorescence microscope in the case of concurrent detection of target nucleic acids. Such fluorophores are selected to have spectral separation of the emissions so that distinct labeling of the target nucleic acids can be detected concurrently. Methods of selecting suitable distinguishable fluorophores for use in methods of the disclosure are well known in the art (see, for example, Johnson and Spence, "*Molecular Probes Handbook, a Guide to Fluorescent Probes and Labeling Technologies,*" 11th ed., Life Technologies (2010)).

Well known methods such as microscopy, cytometry (e.g., mass cytometry, cytometry by time of flight (CyTOF), flow cytometry), or spectroscopy can be utilized to visualize chromogenic, fluorescent, or metal detectable signals associated with the respective target nucleic acids. In general, either chromogenic substrates or fluorogenic substrates, or chromogenic or fluorescent labels, or rare earth metal isotopes, will be utilized for a particular assay, if different labels are used in the same assay, so that a single type of instrument can be used for detection of nucleic acid targets in the same sample.

As disclosed herein, the label can be designed such that the labels are optionally cleavable. As used herein, a cleavable label refers to a label that is attached or conjugated to a label probe so that the label can be removed, for example, in order to use the same label in a subsequent round of labeling and detecting of target nucleic acids. Generally, the labels are conjugated to the label probe by a chemical linker that is cleavable. Methods of conjugating a label to a label probe so that the label is cleavable are well known to those skilled in the art (see, for example, Hermanson, *Bioconjugate Techniques*, Academic Press, San Diego (1996); Daniel et al., *BioTechniques* 24(3):484-489 (1998)). One particular system of labeling oligonucleotides is the FastTag system (Daniel et al., supra, 1998; Vector Laboratories, Burlinghame CA). Various cleavable moieties can be included in the linker so that the label can be cleaved from the label probe. Such cleavable moieties include groups that can be chemically, photochemically or enzymatically cleaved. Cleavable chemical linkers can include a cleavable chemical moiety, such as disulfides, which can be cleaved by reduction, glycols or diols, which can be cleaved by periodate, diazo bonds, which can be cleaved by dithionite, esters, which can be cleaved by hydroxylamine, sulfones, which can be cleaved by base, and the like (see Hermanson, supra, 1996). One particularly useful cleavable linker is a linker containing a disulfide bond, which can be cleaved by reducing the disulfide bond. In other embodiments, the linker can include a site for cleavage by an enzyme. For example, the linker can contain a proteolytic cleavage site. Generally, such a cleavage site is for a sequence-specific protease. Such proteases include, but are not limited to, human rhinovirus 3C protease (cleavage site LEVLFQ/GP), enterokinase (cleavage site DDDDK/), factor $X_a$ (cleavage site IEGR/), tobacco etch virus protease (cleavage site ENLYFQ/G), and thrombin (cleavage site LVPR/GS) (see, for example, Oxford Genetics, Oxford, UK). Another cleavable moiety can be, for example, uracil-DNA (DNA containing uracil), which can be cleaved by uracil-DNA glycosylase (UNG) (see, for example, Sidorenko et al., *FEBS Lett.* 582(3):410-404 (2008)).

The cleavable labels can be removed by applying an agent, such as a chemical agent or light, to cleave the label and release it from the label probe. As discussed above, useful cleaving agents for chemical cleavage include, but are not limited to, reducing agents, periodate, dithionite, hydroxylamine, base, and the like (see Hermanson, supra, 1996). One useful method for cleaving a linker containing a disulfide bond is the use of tris(2-carboxyethyl)phosphine (TCEP) (see Moffitt et al., *Proc. Natl. Acad. Sci. USA* 113:11046-11051 (2016)). In one embodiment, TCEP is used as an agent to cleave a label from a label probe.

In some embodiments, the method for detecting a target nucleic acid in a cell provided herein comprises a pretreatment step before hybridization of the target probe(s). In some embodiments, the pretreatment step comprises a blocking step where certain blocking agent(s) is/are applied to block certain endogenous components of the cell thus reducing assay background. For example, hydrogen peroxide is a blocking agent when horseradish peroxidase (HRP) is used as detection enzyme in the later steps. Hydrogen peroxide is added to inactivate the endogenous HRP activity in the sample, thus reducing assay background. In a specific embodiment, this blocking step is added as the first step in the pretreatment right after deparaffinization. In some embodiments, the pretreatment step comprises an epitope retrieval step, where certain epitope retrieval buffer(s) can be added to unmask the target nucleic acid. In some embodiments, the epitope retrieval step comprises heating the sample. In some embodiments, the epitope retrieval step comprises heating the sample to 50° C. to 100° C. In one embodiment, the epitope retrieval step comprises heating the sample to about 88° C. In some embodiments, the pretreatment step comprises a permeabilization step to retain the nucleic acid targets in the cell and to permit the target probe(s), signal-generating complex, etc. to enter the cell. In some embodiments, the permeabilization step comprises a digestion with a protease. Detergents (e.g., Triton X-100 or SDS) and Proteinase K can also be used to increase the permeability of the fixed cells. Detergent treatment, usually with Triton X-100 or SDS, is frequently used to permeate the membranes by extracting the lipids. Proteinase K is a nonspecific protease that is active over a wide pH range and is not easily inactivated. It is used to digest proteins that surround the target mRNA. Optimal concentrations and durations of treatment can be experimentally determined as is well known in the art. A cell washing step can follow, to remove the dissolved materials produced in the any steps in the pretreatment step. In some embodiments, the sample is in a formalin-fixed paraffin embedded tissue, a deparaffinization step is needed, when paraffin is removed.

In some embodiments, the method for detecting a target nucleic acid in a cell provided herein comprises a post-fixation step at certain timing. In one embodiment, the post-fixation step is (i) after the first fixation step; and (ii) prior to applying at least one set of one or more target probe(s) capable of hybridizing to the target nucleic acid. In one embodiment, the post-fixation step is (i) after the first fixation step; and (ii) prior to pretreatment step described in the immediately preceding paragraph. In one embodiment, the post-fixation step is (i) after the first fixation step; and (ii) prior to the blocking step described in the immediately preceding paragraph. In one embodiment, the post-fixation step is (i) after the first fixation step; and (ii) prior to the epitope retrieval step described in the immediately preceding paragraph. In one embodiment, the post-fixation step is (i) after the first fixation step; and (ii) prior to the permeabilization step described in the immediately preceding paragraph. In one embodiment, the post-fixation step is (i) after the deparaffinization step; and (ii) prior to the applying at least one set of one or more target probe(s) capable of hybridizing to the target nucleic acid. In one embodiment, the post-fixation step is (i) after the deparaffinization step; and (ii) prior to pretreatment step described in the immediately preceding paragraph. In one embodiment, the post-fixation step is (i) after the deparaffinization step; and (ii) prior to the blocking step described in the immediately preceding paragraph. In one embodiment, the post-fixation step is (i) after the deparaffinization step; and (ii) prior to the epitope retrieval step described in the immediately preceding paragraph. In one embodiment, the post-fixation step is (i) after the deparaffinization step; and (ii) prior to the permeabilization step described in the immediately preceding paragraph.

The methods provided herein have several applications in research and diagnostics (Hanna et al., Frontiers in Genetics, 10, 1-6, 2019; Watts et al., Journal of Pathology, 226(2), 365-379, 2012). The methods provided herein can improve our understanding of small nucleic acids, including sncR-NAs, miRNAs, siRNAs, piRNAs, and ASOs, in their native context and their associated gene regulatory networks that are involved various of healthy stages and disease stages.

In some embodiments, the methods provided herein can detect small RNAs with spatial and temporal resolution. In one embodiment, the methods provided herein can be used for identification of tissues and cell types. In one embodiment, the methods provided herein can be used for identification of different stages of development. In one embodiment, the methods provided herein can be used for characterization of adult tissue.

In some embodiments, the methods provided herein can be used to detect altered small RNA expression or the presence of pathogen-derived small RNAs. In one embodiment, the methods provided herein can be used for diagnosing a disease or disorder. In one embodiment, the methods provided herein can be used for diagnosing pathogen.

In some embodiments, the methods provided herein are to monitor the effectiveness of a small RNA-based therapy. In one embodiment, the methods provided herein are to monitor the effectiveness of siRNA-based therapy. In one embodiment, the methods provided herein are to monitor the effectiveness of ASO-based therapy. In some embodiments, the methods provided herein are to determine the effectiveness of a small RNA-based therapy. In one embodiment, the methods provided herein are to determine the effectiveness of siRNA-based therapy. In one embodiment, the methods provided herein are to determine the effectiveness of ASO-based therapy.

In specific embodiments, the method can be used for detecting the presence of the siRNAs following the delivery of the siRNAs into disease models. In specific embodiments, the method can be used for localizing the siRNAs following the delivery of the siRNAs into disease models. In specific embodiments, the method can be used for quantifying the siRNAs following the delivery of the siRNAs into disease models. In specific embodiments, the method can be used for quantifying the RNAs that the siRNAs target following the delivery of the siRNAs into disease models.

In specific embodiments, the method can be used for detecting the presence of the ASOs following the delivery of the ASOs into disease models. In specific embodiments, the method can be used for localizing the ASOs following the delivery of the ASOs into disease models. In specific embodiments, the method can be used for quantifying the ASOs following the delivery of the ASOs into disease models. In specific embodiments, the method can be used for quantifying the RNAs that the ASOs target following the delivery of the ASOs into disease models.

5.4 A Kit for In Situ Detection of a Target Nucleic Acid

In yet another aspect, provided herein is a kit for performing the various methods described herein.

In some embodiments, provided herein is a kit for in situ detecting a target nucleic acid in a cell, comprising: (i) an agent for fixing a biological sample comprising the cell; (ii) an aldehyde-containing fixative for fixing the biological sample; (iii) an agent for performing in situ hybridization; and (iv) an instruction indicating that the aldehyde-containing fixative is used after the agent in the component (i).

In other embodiments, provided herein is a kit for in situ detecting a target nucleic acid in a cell, comprising: (i) an aldehyde-containing fixative for fixing a biological sample comprising the cell and that has been previously fixed; (ii) an agent for performing in situ hybridization.

In one embodiment, the agent used for fixing a biological sample in the kit is ethanol. In one embodiment, the agent used for fixing a biological sample in the kit is methanol. In one embodiment, the agent used for fixing a biological sample in the kit is acetone. In one embodiment, the agent used for fixing a biological sample in the kit is acetic acid. In one embodiment, the agent used for fixing a biological sample in the kit is zinc chloride. In one embodiment, the agent used for fixing a biological sample in the kit is zinc sulfate. In one embodiment, the agent used for fixing a biological sample in the kit is picric acid. In one embodiment, the agent used for fixing a biological sample in the kit is formaldehyde. In one embodiment, the agent used for fixing a biological sample in the kit is glutaraldehyde. In one embodiment, the agent used for fixing a biological sample in the kit is osmium tetroxide. In some specific embodiments, the agent used for fixing a biological sample in the kit is a type of carbodiimides. In some specific embodiments, the agent used for fixing a biological sample in the kit is a type of diimidoesters. In one embodiment, the agent used for fixing a biological sample in the kit is chloro-s-triazides (cyanuric chloride). In some specific embodiments, the agent used for fixing a biological sample in the kit is a type of diisocyanates. In one embodiment, the agent used for fixing a biological sample in the kit is diethylpyrocarbonate (DPC). In some specific embodiments, the agent used for fixing a biological sample in the kit is a type of maleimides. In one embodiment, the agent used for fixing a biological sample in the kit is benzoquinone. In one embodiment, the agent used for fixing a biological sample in the kit is mercuric chloride. In one embodiment, the agent used for fixing a biological sample in the kit is potassium dichromate. In one embodiment, the agent used for fixing a biological sample in the kit is potassium permanganate. In one embodiment, the agent used for fixing a biological sample in the kit is chromic acid.

In one embodiment, the agent used for fixing a biological sample in the kit is Bouin's fixative, which is a solution of picric acid, formaldehyde, and acetic acid. In one embodiment, the agent used for fixing a biological sample in the kit is Clarke's fixative, which is a solution of ethanol and acetic acid. In one embodiment, the agent used for fixing a biological sample in the kit is Carnoy's fixative, which is a solution of ethanol, chloroform, and acetic acid. In one embodiment, the agent used for fixing a biological sample in the kit is a mixture solution of formaldehyde and glutaraldehyde. In one embodiment, the agent used for fixing a biological sample in the kit is FAA, which is a solution of ethanol, acetic acid, and formaldehyde. In one embodiment, the agent used for fixing a biological sample in the kit is periodate-lysine-paraformaldehyde (PLP), which is a solution of paraformaldehyde, L-lysine, and $INaO_4$. In one embodiment, the agent used for fixing a biological sample in the kit is phosphate buffered formalin (PBF). In one embodiment, the agent used for fixing a biological sample in the kit is formal calcium, which is a solution of formaldehyde and calcium chloride. In one embodiment, the agent used for fixing a biological sample in the kit is formal saline, which is a solution of formaldehyde and sodium chloride. In one embodiment, the agent used for fixing a biological sample in the kit is zinc formalin, which is a solution of formaldehyde and zinc sulphate. In one embodiment, the agent used for fixing a biological sample in the kit is Zenker's fixative, which is a solution of mercuric chloride, potassium dichromate, and glacial acetic acid. In one embodiment, the agent used for fixing a biological sample in the kit is Helly's fixative, which is a solution of formaldehyde, potassium dichromate, sodium sulphate, and mercuric chloride. In one embodiment, the agent used for fixing a biological sample in the kit is B-5 fixative, c mercuric chloride and sodium acetate. In one embodiment, the agent used for fixing a biological sample in the kit is Hollande's fixative, which is a solution of formaldehyde, copper acetate, picric acid, and acetic acid. In one embodiment, the agent used for fixing a biological sample in the kit is Gendre's solution, which is a solution of formaldehyde, ethanol, picric acid, and acetic acid glacial. In one embodiment, the agent used for fixing a biological sample in the kit is Methacarn's fixative, which is a solution of methanol, chloroform, and acetic acid glacial. In one embodiment, the agent used for fixing a biological sample in the kit is alcoholic formalin, which is a solution of formaldehyde, ethanol, and calcium acetate. In one embodiment, the agent used for fixing a biological sample in the kit is formol acetic alcohol, which is a solution of formaldehyde, acetic acid glacial, and ethanol.

In some embodiments, the agent used for fixing a biological sample in the kit is a mixture solution of two, three, four, five, or more fixatives, selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid In some embodiments, the agent used for fixing a biological sample in the kit is two or more fixatives applied not at the same time but consecutively, wherein the two or more fixatives are selected from a list of comprising ethanol, methanol, acetone, acetic acid, zinc chloride, zinc sulfate, picric acid, osmium tetroxide, formaldehyde, glutaraldehyde, carbodiimides, diimidoesters, chloro-s-triazides (cyanuric chloride), diisocyanates, diethylpyrocarbonate (DPC), maleimides, benzoquinone, mercuric chloride, potassium dichromate, potassium permanganate, and chromic acid.

In some embodiments, the agent used for fixing a biological sample in the kit is fixative(s) that is suitable for preserving nucleic acids. In one embodiment, the fixative is FineFix (see Kothmaier et al., Arch. Pathol. Lab. Med. 135:744-752, 2011). In one embodiment, the fixative is Glyo-fix (see Lykidis et al., Nucleic Acids Res. 35:e85, 2007). In one embodiment, the fixative is Histochoice (see Vince et al., Anal. Cell. Pathol. 15:119-129, 1997). In one embodiment, the fixative is HOPE (see Kothmaier et al., Arch. Pathol. Lab. Med. 135:744-752, 2011). In one embodiment, the fixative is Neo-Fix (see Paavilainen et al., Histochem. Cytochem.: Official J. Histochem. Soc. 58:237-246, 2010). In one embodiment, the fixative is the PAXgene Tissue System (see Nietner et al., Int. J. Pathol. 461:259-269, 2012). In one embodiment, the fixative is RCL2 (see van Essen et al., Clin. Pathol. 63:1090-1094, 2010). In one embodiment, the fixative is Streck's Tissue Fixative (see Burns et al., Histochem. Cytochem. 57:257-264, 2009). In one embodiment, the fixative is UMFIX (see Nadji et al., Appl. Immunohistochem. Mol. Morphol. 13:277-282, 2005). In one embodiment, the fixative is Z7 (see Lykidis et al., Nucleic Acids Res. 35:e85, 2007). In one embodiment, the fixative is ZBF (see Paavilainen et al., Histochem. Cytochem.: Official J. Histochem. Soc. 58:237-246, 2010).

The kit provided herein comprises an aldehyde-containing fixative. In one embodiment, the aldehyde-containing fixative in the kit is formaldehyde. In one embodiment, the aldehyde-containing fixative in the kit is glutaraldehyde. In one embodiment, the aldehyde-containing fixative in the kit is Bouin's fixative, which is a solution of picric acid, formaldehyde, and acetic acid. In one embodiment, the aldehyde-containing fixative in the kit is a mixture of formaldehyde and glutaraldehyde. In one embodiment, the aldehyde-containing fixative in the kit is FAA, which is a solution of ethanol, acetic acid, and formaldehyde. In one embodiment, the aldehyde-containing fixative in the kit is periodate-lysine-paraformaldehyde (PLP), which is a solution of paraformaldehyde, L-lysine, and $INaO_4$. In one embodiment, the aldehyde-containing fixative in the kit is phosphate buffered formalin (PBF). In one embodiment, the aldehyde-containing fixative in the kit is formal calcium, which is a solution of formaldehyde and calcium chloride. In one embodiment, the aldehyde-containing fixative in the kit is formal saline, which is a solution of formaldehyde and sodium chloride. In one embodiment, the aldehyde-containing fixative in the kit is zinc formalin, which is a solution of formaldehyde and zinc sulphate. In one embodiment, the aldehyde-containing fixative in the kit is Helly's fixative, which is a solution of formaldehyde, potassium dichromate, sodium sulphate, and mercuric chloride. In one embodiment, the aldehyde-containing fixative in the kit is Hollande's fixative, which is a solution of formaldehyde, copper acetate, picric acid, and acetic acid. In one embodiment, the aldehyde-containing fixative in the kit is Gendre's solution, which is a solution of formaldehyde, ethanol, picric acid, and acetic acid glacial. In one embodiment, the aldehyde-containing fixative in the kit is alcoholic formalin, which is a solution of formaldehyde, ethanol, and calcium acetate. In one embodiment, the aldehyde-containing fixative in the kit is formol acetic alcohol, which is a solution of formaldehyde, acetic acid glacial, and ethanol. In one embodiment, the aldehyde-containing fixative in the kit is a mixture of fixatives, wherein at least one fixative of the mixture is formaldehyde or glutaraldehyde. In one embodiment, the aldehyde-containing fixative in the kit is fixatives that are not used at the same time but consecutively, wherein at least one fixative is formaldehyde or glutaraldehyde.

In some embodiments, the aldehyde-containing fixative in the kit provided herein comprises about 5% to about 50% formaldehyde. In other embodiments, the aldehyde-containing fixative comprises about 10% to about 40% formaldehyde. In yet other embodiments, the aldehyde-containing fixative comprises about 12% to about 37% formaldehyde.

In some embodiments, the aldehyde-containing fixative in the kit provided herein comprises various concentrations of formaldehyde. In one embodiment, the aldehyde-containing fixative comprises about 5% formaldehyde. In one embodiment, the aldehyde-containing fixative comprises about 6% formaldehyde. In one embodiment, the aldehyde-containing fixative comprises about 7% formaldehyde. In one embodiment, the aldehyde-containing fixative comprises about 8% formaldehyde. In one embodiment, the aldehyde-containing fixative comprises about 9% formaldehyde. In one embodiment, the aldehyde-containing fixative comprises about 10% formaldehyde. In one embodiment, the aldehyde-containing fixative comprises about 11% formaldehyde. In one embodiment, the aldehyde-containing fixative comprises about 12% formaldehyde. In one embodiment, the aldehyde-containing fixative comprises about 13% formaldehyde. In one embodiment, the aldehyde-containing fixative comprises about 14% formaldehyde. In one embodiment, the aldehyde-containing fixative comprises about 15% formaldehyde. In one embodiment, the aldehyde-containing fixative comprises about 16% formaldehyde. In one embodiment, the aldehyde-containing fixative comprises about 17% formaldehyde. In one embodiment, the aldehyde-containing fixative comprises about 18% formaldehyde. In one embodiment, the aldehyde-containing fixative comprises about 19% formaldehyde. In one embodiment, the aldehyde-containing fixative comprises about 20% formaldehyde. In one embodiment, the aldehyde-containing fixative comprises about 30% formaldehyde. In one embodiment, the aldehyde-containing fixative comprises about 35% formaldehyde. In one embodiment, the aldehyde-containing fixative comprises about 40% formaldehyde. In one embodiment, the aldehyde-containing fixative comprises about 50% formaldehyde.

In some embodiments, the kit further comprises a tool for obtaining a biological sample from a subject. In certain embodiments, the biological sample is a tissue specimen or is derived from a tissue specimen. In certain embodiments, the biological sample is a blood sample or is derived from a blood sample. In certain embodiments, the biological sample is a cytological sample or is derived from a cytological sample.

In some embodiments, the target nucleic acid is DNA. In some embodiments, the target nucleic acid is RNA. In some embodiments, the target nucleic acid is long RNA. In some embodiments, the target nucleic acid is short RNA. In some embodiments, the target nucleic acid is RNA comprising less than 100 nucleotides. In other embodiments, the target nucleic acid is RNA comprising less than 50 nucleotides. In other embodiments, the target nucleic acid is RNA comprising between 15 and 40 nucleotides. In some embodiments, the target nucleic acid is sncRNA. In other embodiments, the target nucleic acid is miRNA, siRNA, piRNA, or ASO. In yet other embodiments, the target nucleic acid is an endogenous RNA or an exogenous RNA.

In a specific embodiment, the kit provided herein comprises agents for performing RNAscope® as described in more detail in, e.g., U.S. Pat. Nos. 7,709,198, 8,604,182, and 8,951,726. In some embodiments, the kit comprises at least one set of one or more target probe(s) capable of hybridizing to a target nucleic acid; a signal-generating complex capable of hybridizing to said set of one or more target probe(s), wherein said signal-generating complex comprises a label probe and a nucleic acid component capable of hybridizing to said set of one or more target probe(s).

In some embodiments, the target probe(s) comprises a target (T) section and a label (L) section, wherein the T section is a nucleic acid sequence complementary to a section on the target nucleic acid and the L section is a nucleic acid sequence complementary to a section on the nucleic acid component of the signal-generating complex, and wherein the T sections of the one or more target probe(s) are complementary to non-overlapping regions of the target nucleic acid, and the L sections of the one or more target probe(s) are complementary to non-overlapping regions of the nucleic acid component of the generating complex.

In some embodiments, the kit further comprises signal-generating complex as described in Section 5.3 above, which may incudes label probe, amplifier, pre-amplifier, and/or pre-pre-amplifier.

In some embodiments, the kit further comprises other agents or materials for performing RNA ISH, including fixing agents and agents for treating samples for preparing hybridization, agents for washing samples, and so on.

The kit may further comprise "packaging material" which refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits provided herein can include labels or inserts. Labels or inserts include information on a condition, disorder, disease, or symptom for which the kit component may be used for. Labels or inserts can include instructions for a clinician or for a subject to use one or more of the kit components in a method, treatment protocol, or therapeutic regimen. In some embodiments, the kit can be used for identification of tissues and cell types. In some embodiments, the kit can be used for identification of different stages of development. In some embodiments, the kit can be used for detection of clinical biomarkers for cancers. In some embodiments, the kit can be used for diagnosing a disease or disorder based on the expression of one or more altered small RNAs or the presence of pathogen-derived small RNAs. In some embodiments, the kit can be used for characterization of adult tissue. In some embodiments, the kit can be used for detection of clinical biomarkers for pathogen diagnosis. In some embodiments, the kit can be used for detection and characterization of small RNA-based therapies. In some embodiments, the kit can be used for confirmation of the initial efficiency of small RNA-based therapies. In some embodiments, the kit can be used to continue monitoring the efficiency of small RNA-based therapies. In some embodiments, the kit can be used for determining the efficiency of small RNA-based therapies. In some embodiments, the kit can be used for detecting the presence, localizing, and quantifying siRNAs. In some embodiments, the kit can be used for detecting the presence, localizing, and quantifying ASO molecules. In some embodiments, the kit can be used for detection and identification of pathogen-derived small RNAs.

6. EXAMPLES

The following is a description of various methods and materials used in the studies, and are put forth so as to provide those of ordinary skill in the art with a complete disclosure and description of how to make and use the present disclosure, and are not intended to limit the scope of what the inventors regard as their disclosure nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present disclosure. Efforts have been made to ensure accuracy with respect to numbers used (e.g., amounts, percentages, etc.), but some experimental errors and deviations should be accounted for.

6.1 Integration of the Post-Fixation Strategy for Small Nucleic Acid Preservation in a Standard RNA ISH Workflow Conventionally preserved biological specimens follow a standard deparaffinization process where samples are heated to melt the paraffin wax and then undergo a series of xylene and ethanol washes to remove all traces of wax. This process leads to small nucleic acid loss. To minimize the loss by diffusion during the sample pretreatment and hybridization/washing steps, specimens are post-fixed using an aldehyde-containing fixative for a minimum of 2 hours at ambient temperature prior to sample pretreatment. Minimal retention of these nucleic acid species was observed in samples post-fixed for periods less than two hours long. Optimal retention was observed between 2 to 18 hours post-fixation contingent upon the fixative employed. Biological specimens post-fixed with formaldehyde at concentrations equal to or higher than about 12% only required a short (2-hour) exposure to the fixative while concentration lower than about 12% formaldehyde, such as 10% Neutral Buffered Formalin or NBF, required extended (18 hours) treatment. Samples that followed the post-fixation workflow are fully compatible with subsequent steps in the outlined universal ISH workflow, which include sample pretreatment, target probe hybridization, and detection.

6.2 Post-Fixation with Formaldehyde Concentrations Equal or Higher than 12% for Detection of miRNA Post-fixation with formaldehyde minimizes miRNA loss and improves detection sensitivity by RNAscope® ISH. Mouse formalin-fixed paraffin embedded tissue sections were untreated or post-fixed with a range of formaldehyde concentrations from about 12% to about 37% prepared in 1×PBS for 2 hours at ambient temperature. Formaldehyde concentrations equal or higher than about 12% result in maximal retention of miRNAs when post-fixed for 2 hours. Specific miRNAs were detected using the RNAscope® 2.5 High Definition (HD)-Red Assay following established conditions for formalin-fixed paraffin embedded tissue processing. ISH signal appears as punctate dots and hematoxylin stains individual nuclei. As shown in FIG. 2A, heart-enriched miR-1a-3p was detected following post-fixation process. As shown in FIG. 2B, brain-enriched miR-132-3p was detected following post-fixation process. In the absence of post-fixation, miRNAs diffuse from the tissue and are undetectable, as evidence by the lack of punctate dots in heart and brain tissue. In contrast, dot formation is observed within post-fixed tissues, demonstrating the effectiveness of the disclosure herein. No additional benefits on miRNA detection sensitivity were observed when increasing the concentration of formaldehyde from 12% to 37% as similar punctate dot number was overserved across the tissues.

6.3 Post-Fixation with 10% NBF for Detection of miRNA

Mouse formalin-fixed paraffin embedded tissue sections were untreated or post-fixed with 10% NBF, the most commonly used aldehyde-containing fixative with approximately 4% formaldehyde content prepared in distilled water and sodium phosphate to neutral pH, for 18 hours at ambient temperature. Shorter incubation periods result in suboptimal miRNA retention in tissues. Heart-enriched miR-1a-3p (FIG. 3A), brain-enriched miR-132-3p (FIG. 3B), liver-enriched miR-122-5p (FIG. 3C), and ubiquitously expressed let-7 (FIG. 3D) were detected by RNAscope® 2.5 High Definition (HD)-Red Assay following established conditions for formalin-fixed paraffin embedded tissue processing. Incorporating a post-fixation step in an ISH assay leads to exceptional small nucleic acid detection sensitivity (shown as punctate dot formation) compared to tissues left untreated.

6.4 Post-Fixation with Formaldehyde for Detection of Long RNA Species

Post-fixation workflow has been shown to be fully compatible with detection of long RNA species. Human and mouse formalin-fixed paraffin embedded tissues were untreated or post-fixed with 10% NBF and continued with the universal ISH workflow outlined in FIG. 1. As shown in FIG. 4A, human TATA-box-binding protein (TBP) mRNA was detected in human skin A431 cells that were untreated or NBF-post fixed using the RNAscope® 2.5 High Definition (HD)-Red Assay. Mouse polymerase RNA II polypeptide A (POLR2A) mRNA was detected in mouse intestine (FIG. 4B) and brain tissue (FIG. 4C), respectively, using the RNAscope® 2.5 High Definition (HD)-Red Assay. Similar detection sensitivity of long RNA species was observed between untreated and post-fixed tissues, suggesting though small RNA species preferentially benefit from this alternative ISH workflow, detection of long RNA species will not be compromised by this alternative ISH workflow.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method for preparing a biological sample for in situ hybridization, the method comprising:
   (i) a first fixation step comprising fixing the biological sample with an agent; and

54

(ii) a post-fixation step after the first fixation step and prior to the in situ hybridization comprising fixing the biological sample with a formaldehyde-containing fixative:
      (a) for about 2 to 18 hours at ambient temperature, wherein the formaldehyde-containing fixative comprises at least about 12% formaldehyde, or
      (b) for about 18 hours at ambient temperature, wherein the formaldehyde-containing fixative comprises less than about 12% formaldehyde;
   wherein the in situ hybridization detects a nucleic acid comprising 100 nucleotides or less in the biological sample.

2. The method of claim 1, wherein the in situ hybridization is RNA in situ hybridization or DNA in situ hybridization.

3. The method of claim 2, wherein the in situ hybridization is RNA in situ hybridization that detects RNA comprising between 15 and 40 nucleotides.

4. The method of claim 2, wherein the in situ hybridization is RNA in situ hybridization that detects small non-coding RNAs (sncRNAs).

5. The method of claim 2, wherein the RNA in situ hybridization or the DNA in situ hybridization detects microRNA (miRNA), small interfering RNA (siRNA), PIWI-interacting RNA (piRNA), or antisense oligonucleotides (ASO) molecules, and wherein the RNA in situ hybridization or the DNA in situ hybridization detects an endogenous or an exogenous nucleic acid.

6. The method of claim 1, wherein the biological sample: is a tissue specimen or is derived from a tissue specimen; is a blood sample or is derived from a blood sample; is a cytological sample or is derived from a cytological sample; or comprises cultured cells or an exosome.

7. The method of claim 1, wherein the agent in the first fixation step is selected from a group consisting of formaldehyde, glutaraldehyde, methanol, ethanol, and acetone.

8. The method of claim 1, wherein the formaldehyde-containing fixative comprises at least about 12% formaldehyde, and wherein the post-fixation step comprises fixing the biological sample with the formaldehyde-containing fixative for about 2 hours.

9. The method of claim 1, wherein the formaldehyde-containing fixative comprises about 12% to about 37% formaldehyde, and wherein the post-fixation step comprises fixing the biological sample with the formaldehyde-containing fixative for about 2 hours.

10. The method of claim 1, wherein the formaldehyde-containing fixative in the post-fixation step comprises an additional agent in addition to formaldehyde.

11. A method for detecting a target nucleic acid in a cell, comprising:
   (i) preparing a biological sample according to the method of claim 1;
   (ii) providing at least one set of one or more target probe(s) capable of hybridizing to said target nucleic acid;
   (iii) providing a signal-generating complex capable of hybridizing to said set of one or more target probe(s), wherein said signal-generating complex comprises a nucleic acid component capable of hybridizing to said set of one or more target probe(s) and a label probe;
   (iv) hybridizing said target nucleic acid to said set of one or more target probe(s); and
   (v) capturing the signal-generating complex to said set of one or more target probe(s) and thereby capturing the signal-generating complex to said target nucleic acid.

12. The method of claim 1, wherein the method is used to: identify a tissue or cell type; to determine a developmental stage; to characterize adult tissue; to diagnose a disease or disorder based on the expression of one or more altered small RNAs or the presence of pathogen-derived small RNAs; to diagnose a disease or disorder based on the expression of one or more altered small RNAs or the presence of pathogen-derived small RNAs; or to monitor or determine the effectiveness of a small RNA-based therapy.

13. A method of in situ detection of a target nucleic acid in a previously fixed sample, the method comprising:
  (i) applying a formaldehyde-containing fixative to the previously fixed sample:
    (a) for about 2 to 18 hours at ambient temperature, wherein the formaldehyde-containing fixative comprises at least about 12% formaldehyde, or
    (b) for at least 18 hours at ambient temperature, wherein the formaldehyde-containing fixative comprises less than about 12% formaldehyde; and
  ii) conducting an in situ hybridization detection assay with a set of one or more probes hybridizing to the target nucleic acid;
  wherein the target nucleic acid comprises less than 100 nucleotides.

14. The method of claim 13, wherein the in situ hybridization is RNA in situ hybridization or DNA in situ hybridization.

15. The method of claim 14, wherein the in situ hybridization is RNA in situ hybridization that detects RNA comprising between 15 and 40 nucleotides.

16. The method of claim 14, wherein the in situ hybridization is RNA in situ hybridization that detects small non-coding RNAs (sncRNAs).

17. The method of claim 14, wherein the RNA in situ hybridization or the DNA in situ hybridization detects microRNA (miRNA), small interfering RNA (siRNA), PIWI-interacting RNA (piRNA), or antisense oligonucleotides (ASO) molecules, and wherein the RNA in situ hybridization or the DNA in situ hybridization detects an endogenous or an exogenous nucleic acid.

18. The method of claim 13, wherein the sample: is a tissue specimen or is derived from a tissue specimen; is a blood sample or is derived from a blood sample; is a cytological sample or is derived from a cytological sample; or comprises cultured cells or an exosome.

* * * * *